United States Patent
Popp et al.

(10) Patent No.: US 10,076,453 B2
(45) Date of Patent: *Sep. 18, 2018

(54) BODY ATTACHED ABSORBENT ARTICLE DONNING SYSTEM

(71) Applicant: Kimberly-Clark Worldwide, Inc., Neenah, WI (US)

(72) Inventors: Robert Lee Popp, Greenville, WI (US); Thomas Harold Roessler, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 491 days.

This patent is subject to a terminal disclaimer.

(21) Appl. No.: 14/820,187

(22) Filed: Aug. 6, 2015

(65) Prior Publication Data

US 2015/0335499 A1  Nov. 26, 2015

Related U.S. Application Data

(62) Division of application No. 13/224,523, filed on Sep. 2, 2011, now Pat. No. 9,132,049.

(51) Int. Cl.
| | | |
|---|---|---|
| *A61F 13/15* | (2006.01) | |
| *A61F 13/20* | (2006.01) | |
| *A61F 13/56* | (2006.01) | |
| *A61F 13/472* | (2006.01) | |
| *A61F 13/511* | (2006.01) | |
| *A61F 13/60* | (2006.01) | |

(Continued)

(52) U.S. Cl.
CPC ........ *A61F 13/5605* (2013.01); *A61F 13/472* (2013.01); *A61F 13/5116* (2013.01); *A61F 13/60* (2013.01); *A61F 13/82* (2013.01); *A61F 2013/16* (2013.01); *A61F 2013/51333* (2013.01); *A61F 2013/51383* (2013.01)

(58) Field of Classification Search
CPC ...... A61F 13/82; A61F 13/5605; A61F 13/58; A61F 2013/583; A61F 13/51478; A61F 13/505; A61F 13/15; D10B 2509/026
USPC .... 604/378, 385.01, 385.03, 385.11, 385.14, 604/385.16, 386–387, 389–390, 393, 397, 604/398, 400–402
See application file for complete search history.

(56) References Cited

U.S. PATENT DOCUMENTS

| | | |
|---|---|---|
| 2,226,546 A | 12/1940 | Bower |
| 2,714,889 A | 8/1955 | Chambers |
| 2,725,332 A | 11/1955 | Allen |

(Continued)

FOREIGN PATENT DOCUMENTS

| | | |
|---|---|---|
| DE | 102006006879 A1 | 8/2007 |
| EP | 0 749 742 A2 | 12/1996 |

(Continued)

*Primary Examiner* — Michele M Kidwell
(74) *Attorney, Agent, or Firm* — Kimberly-Clark Worldwide, Inc.

(57) ABSTRACT

An absorbent article has attachment regions having body adhesive. The attachment regions have a protected condition where the body adhesive is fully covered. The attachment regions are adapted to transition from the protected condition to a fixed donning condition where a portion of the body adhesive is exposed and a portion of the body adhesive is covered. The attachment regions are adapted to transition from the fixed donning condition to a fully exposed condition where the body adhesive is fully exposed.

18 Claims, 15 Drawing Sheets

(51) Int. Cl.
*A61F 13/82* (2006.01)
*A61F 13/513* (2006.01)

(56) References Cited

U.S. PATENT DOCUMENTS

| | | | |
|---|---|---|---|
| 2,742,903 A | 4/1956 | Lightner |
| 3,185,394 A | 5/1965 | Farrell |
| 4,072,151 A | 2/1978 | Levine |
| 4,484,919 A | 11/1984 | Sohn et al. |
| 4,556,146 A | 12/1985 | Swanson et al. |
| 4,753,648 A | 6/1988 | Jackson |
| 4,804,380 A | 2/1989 | Lassen et al. |
| 4,917,675 A | 4/1990 | Taylor et al. |
| 5,088,993 A | 2/1992 | Gaur |
| D337,638 S | 7/1993 | Andrews |
| 5,413,568 A | 5/1995 | Roach et al. |
| 5,569,228 A | 10/1996 | Byrd et al. |
| 5,658,270 A | 8/1997 | Lichstein |
| 5,954,201 A | 9/1999 | Finch et al. |
| 5,967,009 A | 10/1999 | Truttmann et al. |
| 6,074,376 A | 6/2000 | Mills |
| 6,279,440 B1 | 8/2001 | Truttmann et al. |
| 6,298,760 B1 | 10/2001 | Truttmann et al. |
| 6,305,260 B1 | 10/2001 | Truttmann et al. |
| 6,464,821 B1 | 10/2002 | Phillips et al. |
| 6,500,160 B2 | 12/2002 | Mizutani et al. |
| 6,632,210 B1 | 10/2003 | Glasgow et al. |
| 6,997,915 B2 | 2/2006 | Gell et al. |
| 7,122,022 B2 | 10/2006 | Drevik |
| 7,125,401 B2 | 10/2006 | Yoshimasa |
| 7,927,322 B2 | 4/2011 | Cohen et al. |
| 7,947,027 B2 | 5/2011 | Vandenbogart et al. |
| 8,012,137 B2 | 9/2011 | Lira et al. |
| 8,029,489 B2 | 10/2011 | Yu et al. |
| 8,292,862 B2 | 10/2012 | Dennis et al. |
| 8,460,260 B2 | 6/2013 | Fung et al. |
| D698,298 S | 1/2014 | Cortes |
| 8,764,922 B2 | 7/2014 | Popp et al. |
| 8,911,772 B2 | 12/2014 | Sahm et al. |
| 2003/0097111 A1 | 5/2003 | Lundin |
| 2006/0264884 A1 | 11/2006 | Carstens |
| 2007/0016123 A1 | 1/2007 | Jensen |
| 2007/0124850 A1 | 6/2007 | Buettner |
| 2007/0197991 A1 | 8/2007 | Wetter et al. |
| 2008/0095978 A1 | 4/2008 | Siqueira et al. |
| 2009/0036858 A1 | 2/2009 | Van Den Bogart et al. |
| 2009/0069780 A1 | 3/2009 | Plentovich et al. |
| 2009/0182296 A1 | 7/2009 | Dennis et al. |
| 2009/0198203 A1 | 8/2009 | Lira et al. |
| 2009/0204090 A1 | 8/2009 | Dennis et al. |
| 2009/0204092 A1 | 8/2009 | Loyd et al. |
| 2010/0057034 A1 | 3/2010 | Dennis et al. |
| 2010/0082008 A1 | 4/2010 | Gagliardi et al. |
| 2010/0121304 A1 | 5/2010 | Zhou et al. |
| 2010/0152687 A1 | 6/2010 | Carlozzi |
| 2010/0152693 A1 | 6/2010 | Lira et al. |
| 2010/0198177 A1 | 8/2010 | Yahiaoui et al. |
| 2010/0256585 A1 | 10/2010 | Konawa |
| 2010/0280467 A1 | 11/2010 | Uematsu |
| 2012/0199268 A1 | 8/2012 | Popp et al. |
| 2012/0203192 A1 | 8/2012 | Dennis et al. |

FOREIGN PATENT DOCUMENTS

| | | |
|---|---|---|
| EP | 0 750 892 A2 | 1/1997 |
| GB | 2 148 125 | 5/1985 |
| KR | 10-2007-0065594 A | 6/2007 |
| WO | WO 1995/030395 A1 | 11/1995 |
| WO | WO 2000/037015 A1 | 6/2000 |
| WO | WO 2006/111436 A1 | 10/2006 |

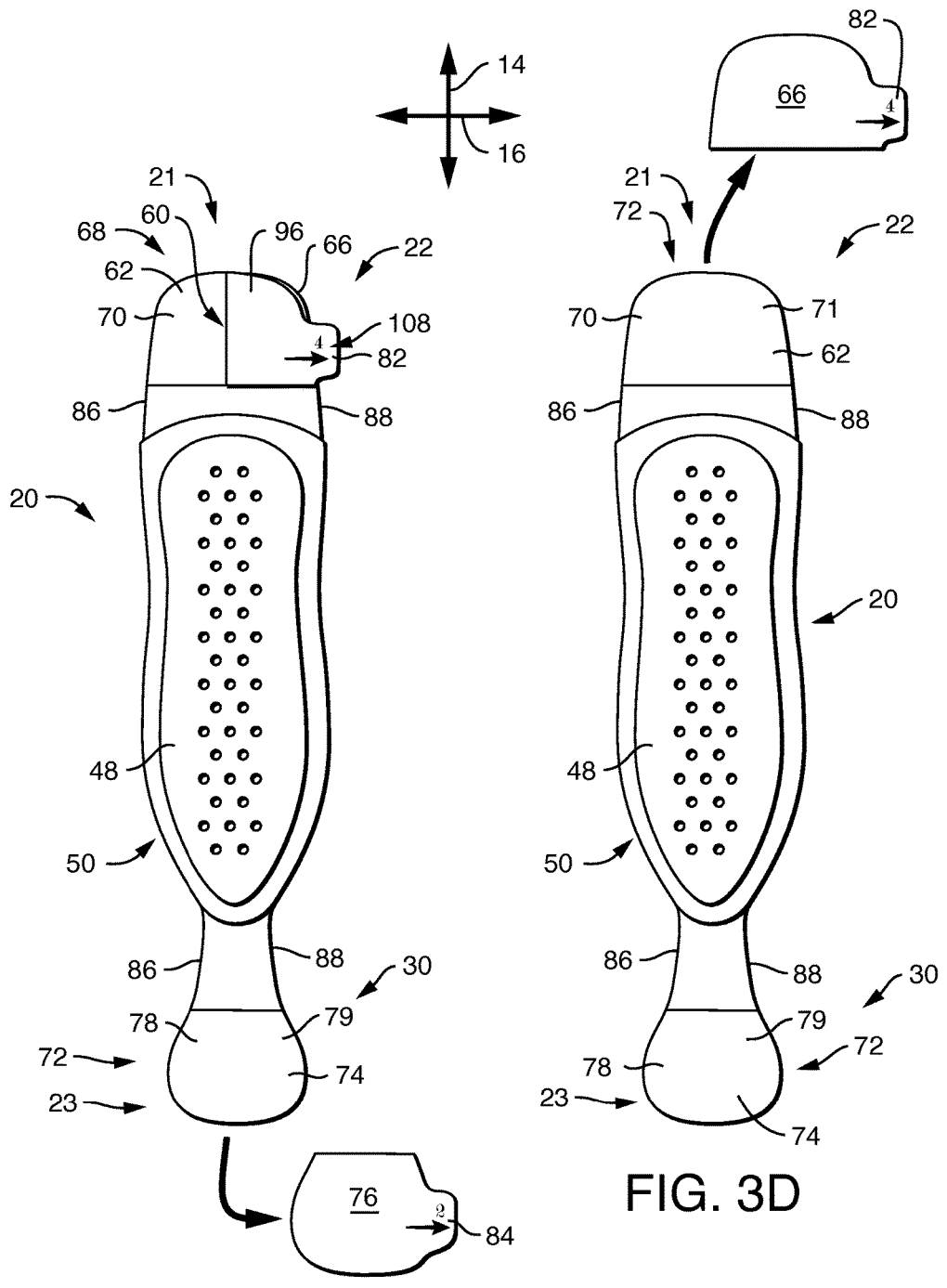

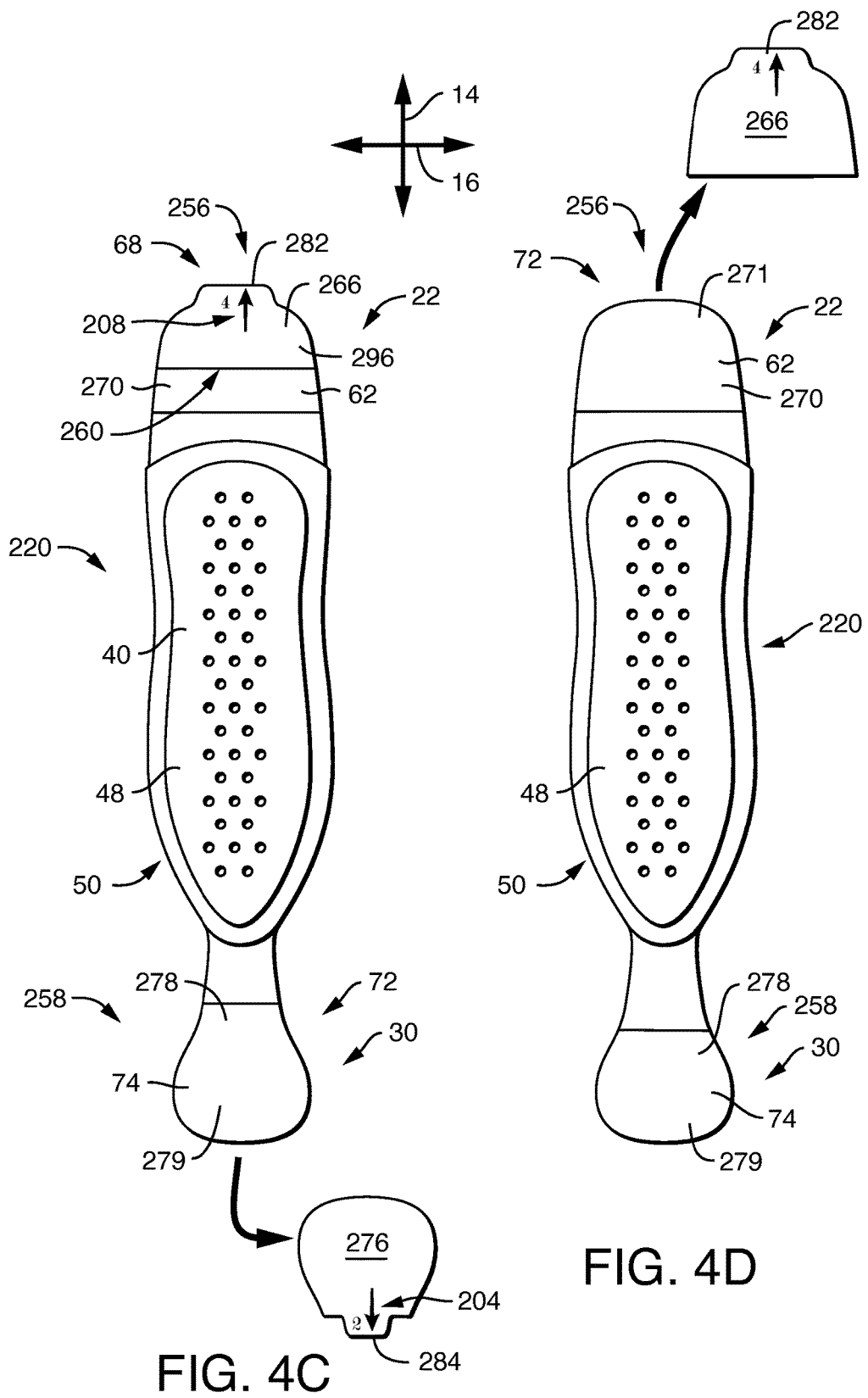

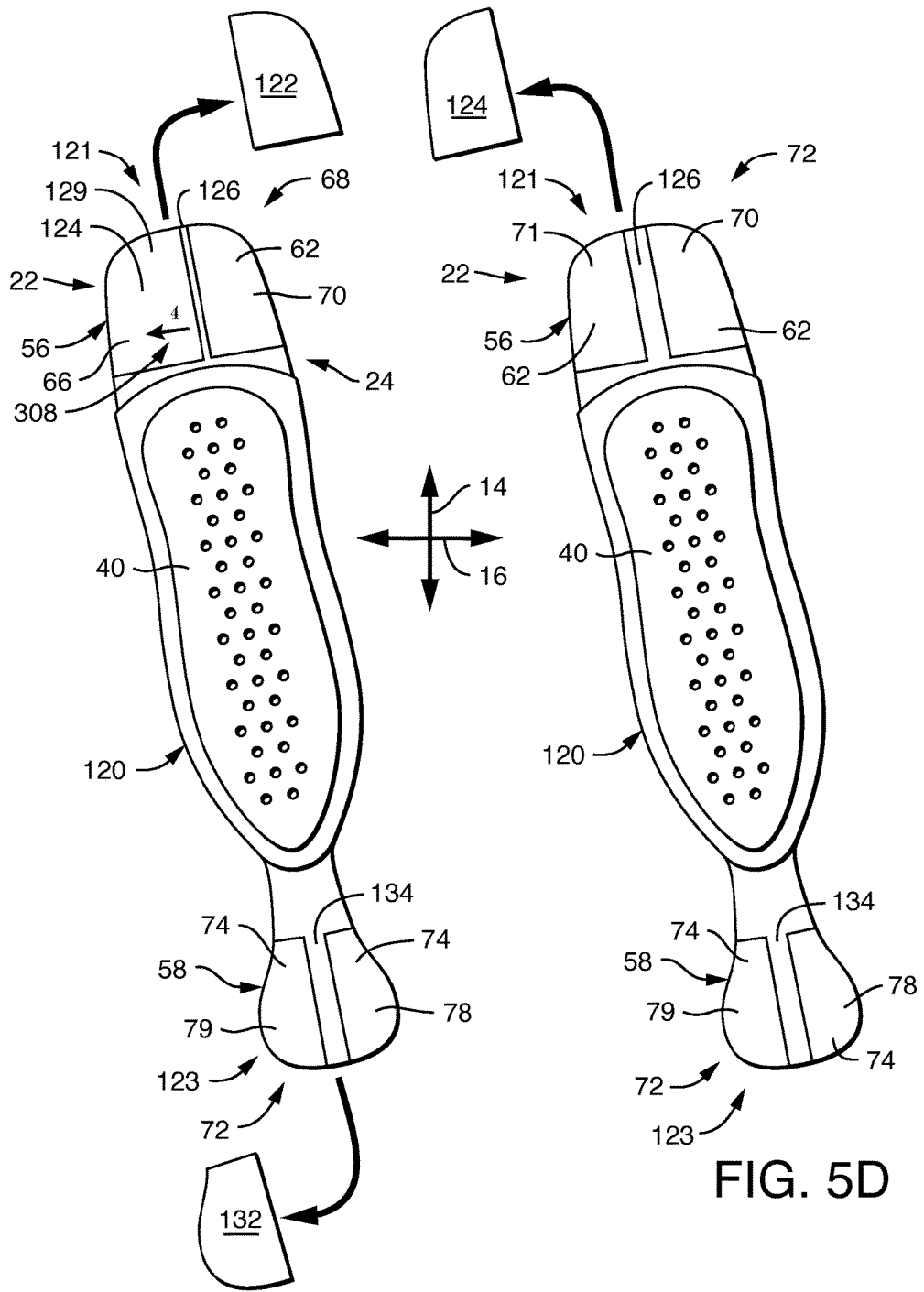

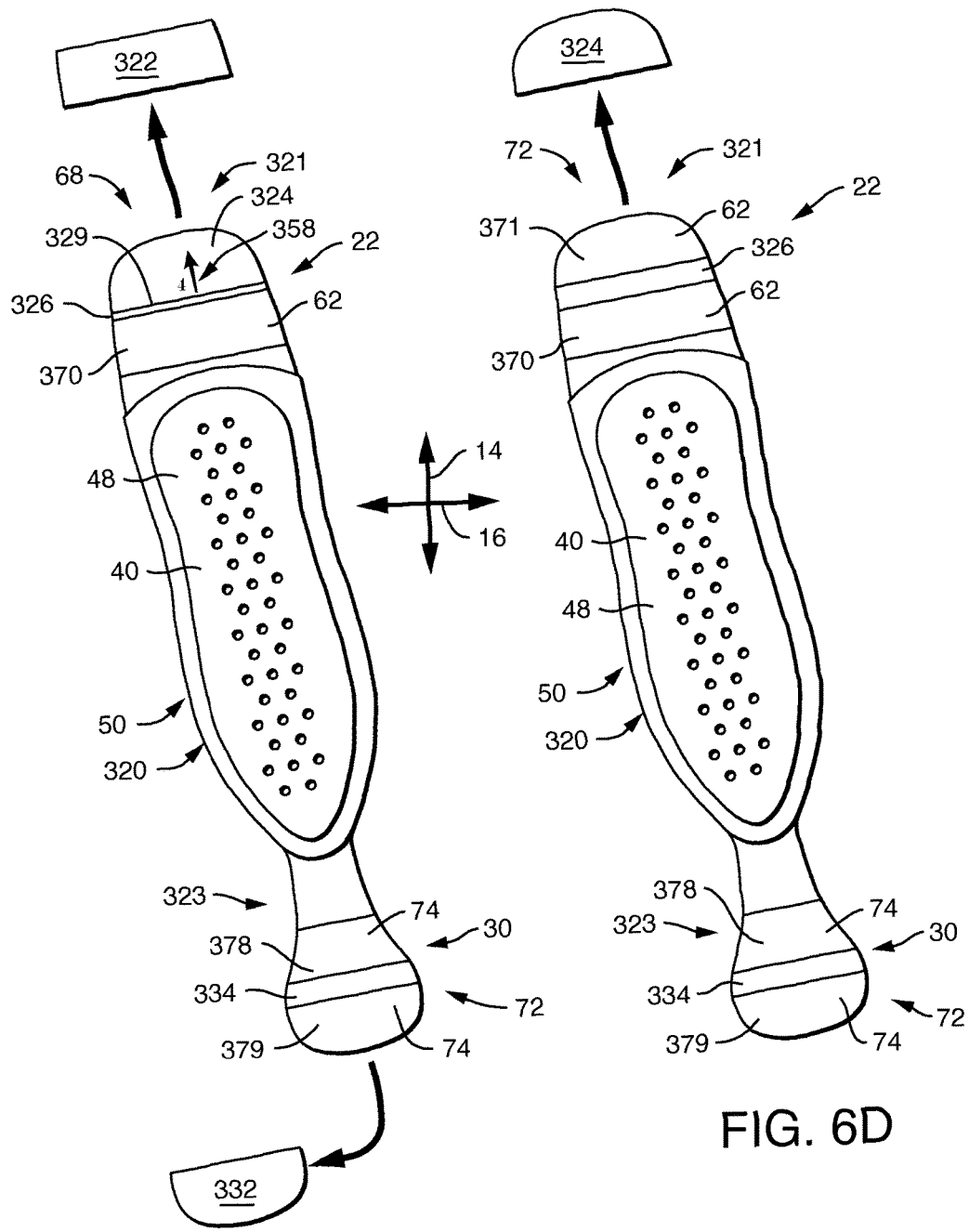

BODY ATTACHED ABSORBENT ARTICLE DONNING SYSTEM

PRIORITY

This application is a divisional of application Ser. No. 13/224,523, entitled "BODY ATTACHED ABSORBENT ARTICLE DONNING SYSTEM" and filed in the U.S. Patent and Trademark Office on Sep. 2, 2011. The entirety of the prior application is hereby incorporated by reference in this application.

BACKGROUND OF THE INVENTION

Body adhering absorbent articles adapted for use as feminine hygiene articles have been previously disclosed. These feminine hygiene articles generally include body adhesive applied to the body-side surface of the absorbent article and are adapted to attach directly to the wearer's skin. However, in some cases, the body adhesive can become contaminated during storage and/or application to the body.

To avoid contaminating the adhesive during storage and before application, the body adhesive is usually covered by one or more peel strips. These peel strips are removed prior to application. The peel strip removal usually involves grasping an edge of the peel strip or a finger tab between the thumb and forefinger and completely removing the peel strip from the absorbent article. Removal of the peel strip consequently exposes the attachment zone and the body attachment adhesive disposed thereon.

Typically, the user then grasps the attachment zone by placing their thumb on the body attachment adhesive and their forefinger on the adjacent shell surface. The product is then positioned and attached to the body. While this traditional product form and method for applying to the body provides suitable function, there are some aspects that can be improved.

For example, the above described donning process can lead to adhesive contamination. Specifically, when the user touches the body attachment adhesive, any oil, lotion, or other contaminates that are present on the skin of the hand of the wearer may be transferred to the body attachment adhesive, which in turn may reduce its effectiveness. Since the donning process frequently takes place immediately after removal of a previously used product and before the opportunity to wash hands, the skin of the hand may also include other contaminating body exudates.

Additionally, previously disclosed body-adhering articles and donning processes may increase the likelihood of errant attachment. Errant attachment is especially problematic because of the size and flexibility of the product and the region of the body where the product needs to be attached. For example, errant attachment may occur if the body adhesive contacts clothing during the donning process or the body adhesive is improperly positioned on the body. Errant attachment may also occur if exposed adhesive folds over onto itself. At best, this requires separation of the attached pieces with some loss of adhesion. At worse, the folded over section cannot be corrected and may result in a product being unfit for use.

SUMMARY OF THE INVENTION

In one aspect, the present invention provides an absorbent article having a shell and an absorbent component. The shell defines, in a longitudinal direction, an anterior attachment region, an anterior separation zone, an absorbent component region, a posterior separation zone, and a posterior attachment region. The anterior separation zone separates the anterior attachment region from the absorbent component region and the posterior separation zone separates the posterior attachment region from the absorbent component region. The anterior attachment region includes an anterior body adhesive and defines a protected condition where the anterior body adhesive is fully covered by one or more anterior peel strips. The anterior attachment region is adapted to transition from the protected condition to a fixed donning condition. In the fixed donning condition a portion of the anterior body adhesive is exposed and a portion of the anterior body adhesive is covered by the one or more anterior peel strips. The anterior attachment region is adapted to transition from the fixed donning condition to a fully exposed condition. In the fully exposed condition the anterior body adhesive is fully exposed.

The posterior attachment region includes a posterior body adhesive and defines a protected condition where the posterior body adhesive is fully covered by one or more posterior peel strips. The posterior attachment region is adapted to transition from the protected condition to a fixed donning condition. In the fixed donning condition a portion of the posterior body adhesive is exposed and a portion of the posterior body adhesive is covered by the one or more posterior peel strips. The posterior attachment region is adapted to transition from the fixed donning condition to a fully exposed condition. In the fully exposed condition the posterior body adhesive is fully exposed. The anterior separation zone and the posterior separation zone are devoid of absorbent material and body adhesive.

In various embodiments, the shell defines a shell length, the anterior separation zone defines an anterior separation zone length, the posterior separation zone defines a posterior separation zone length, and at least one of the anterior separation zone length or the posterior separation zone length is at least 5% of the shell length.

In some embodiments, the shell length is 325 to 350 mm, the anterior separation zone length is 5 to 15 mm, and the posterior separation zone length is 20 to 50 mm.

In some embodiments, the anterior separation zone is elastic, the posterior separation zone is elastic, the anterior attachment region is inelastic, and the posterior attachment region is inelastic.

In some embodiments, the anterior attachment region includes an anterior peel strip with an anterior finger tab and an anterior hinge. A first portion of the anterior peel strip is folded along the anterior hinge to overlay a second portion of the anterior peel strip to define the fixed donning condition. Additionally, the posterior attachment region includes a posterior peel strip with a posterior finger tab and a posterior hinge. A first portion of the posterior peel strip is folded along the posterior hinge to overlay a second portion of the posterior peel strip to define the fixed donning condition. In some embodiments, the anterior finger tab extends from a first longitudinal edge of the absorbent article in the protected condition, the anterior tab extends from a second longitudinal edge of the absorbent article in the fixed donning condition, and the anterior hinge and the posterior hinge are oriented in the longitudinal direction.

In some embodiments, the anterior attachment region includes a first anterior peel strip overlaying a first anterior portion of the anterior body adhesive and a second anterior peel strip overlaying a second anterior portion of the anterior body adhesive to define the protected condition. Additionally, the anterior attachment region includes an anterior adhesive-free portion where the first anterior peel strip overlaps the second anterior peel strip at the anterior adhesive-free portion. In these embodiments, the posterior attachment region includes a first posterior peel strip overlaying a first posterior portion of the posterior body adhesive and a second posterior peel strip overlaying a second posterior portion of the posterior body adhesive to define the protected condition. Additionally, the posterior attachment region includes a posterior adhesive-free portion where the first posterior peel strip overlaps the second posterior peel strip at the posterior adhesive-free portion.

In some embodiments, the absorbent article defines a body-facing surface and a garment-facing surface and the anterior attachment region includes an anterior body adhesive disposed on the body-facing surface and an anterior peel strip overlaying the anterior body adhesive. The anterior peel strip defines a body adhesive facing surface and an opposite surface and includes an anterior anchor attached to the opposite surface of the anterior peel strip. Additionally, the posterior attachment region includes a posterior body adhesive disposed on the body-facing surface and a posterior peel strip overlaying the posterior body adhesive. The posterior peel strip defines a body adhesive facing surface and an opposite surface and includes a posterior anchor attached to the opposite surface of the posterior peel strip. Additionally, the absorbent article includes a longitudinal fold where a first anterior portion of the opposite surface of the anterior peel strip is attached to a second anterior portion of the opposite surface of the anterior peel strip via the anterior anchor and a first posterior portion of the opposite surface of the posterior peel strip is attached to a second posterior portion of the opposite surface of the posterior peel strip via the posterior anchor to define the protected condition.

In some embodiments, the absorbent article defines a body-facing surface and a garment-facing surface and the anterior attachment region includes an anterior body adhesive disposed on the body-facing surface, an anterior peel strip overlaying the anterior body adhesive, the anterior peel strip defining a body adhesive facing surface and an opposite surface, and an anterior anchor disposed on the opposite surface. Additionally, the posterior attachment region includes a body adhesive disposed on the body-facing surface, a posterior peel strip overlaying the posterior body adhesive, the posterior peel strip defining a body adhesive facing surface and an opposite surface, and a posterior anchor disposed on the opposite surface. The absorbent article also includes an anterior lateral fold where a first portion of the absorbent article in the anterior region is folded upon a second portion of the absorbent article in the anterior region along the first anterior lateral fold and a first portion of the opposite surface of the anterior peel strip is attached to a second portion of the opposite surface of the anterior peel strip via the anterior anchor. The absorbent article also includes a posterior lateral fold wherein a first portion of the absorbent article in the posterior region is folded upon a second portion of the absorbent article in the posterior region along the second lateral fold and a first portion of the opposite surface of the posterior peel strip is attached to a second portion of the opposite surface of the posterior peel strip via the posterior anchor.

In another aspect, the present invention provides an absorbent article defining a body-facing surface and a garment-facing surface. The absorbent article includes an anterior attachment region having an anterior body adhesive disposed on the body-facing surface and having an anterior peel strip overlaying the anterior body adhesive. The absorbent article also includes a posterior attachment region having a posterior body adhesive disposed on the body-facing surface and having a posterior peel strip overlaying the posterior body adhesive. At least one of the anterior peel strip and the posterior peel strip includes a hinge. At least one of the anterior peel strip and the posterior peel strip also includes a finger tab that extends beyond the respective attachment region. The at least one of the anterior peel strip and the posterior peel strip is adapted to fold along the hinge to expose a portion of the body adhesive.

In various embodiments, the anterior peel strip includes an anterior hinge and the posterior peel strip includes a posterior hinge.

In some embodiments, the anterior peel strip includes an anterior finger tab and the posterior peel strip includes a posterior finger tab.

In another aspect, the present invention provides an absorbent article defining a body-facing surface and a garment facing surface. The absorbent article includes at least one anterior attachment region or posterior attachment region. The anterior attachment region includes an anterior body adhesive disposed on the body-facing surface and a first anterior peel strip overlaying a first anterior portion of the anterior body adhesive and a second anterior peel strip overlaying a second anterior portion of the anterior body adhesive. The anterior attachment region includes an anterior adhesive-free portion and the first anterior peel strip overlaps the second anterior peel strip at the anterior adhesive-free portion. The posterior attachment region includes a posterior body adhesive disposed on the body-facing surface and a first posterior peel strip overlaying a first posterior portion of the posterior body adhesive and a second posterior peel strip overlaying a second posterior portion of the posterior body adhesive. The posterior attachment region includes a posterior adhesive-free portion and the first posterior peel strip overlaps the second posterior peel strip at the posterior adhesive-free portion. In some embodiments, the absorbent article includes both the anterior attachment region and the posterior attachment region.

In another aspect, the present invention provides an absorbent article defining a body-facing surface and a garment facing surface. The absorbent article includes an anterior attachment region having an anterior body adhesive disposed on the body-facing surface and having an anterior peel strip overlaying the anterior body adhesive. The anterior peel strip defines a body adhesive facing surface and an opposite surface. The opposite surface includes an anterior anchor. The absorbent article also includes a posterior attachment region having a posterior body adhesive disposed on the body-facing surface and having a posterior peel strip overlaying the posterior body adhesive. The posterior peel strip defines a body adhesive facing surface and an opposite surface. The opposite surface includes a posterior anchor. The absorbent article also includes a first lateral portion that includes a shell and an absorbent component. The absorbent article also includes a second lateral portion that includes the shell and the absorbent component. The absorbent article also includes a longitudinal fold where the first lateral portion is in facing relation with the second lateral portion and where a first anterior portion of the opposite surface of the anterior peel strip is attached to a second anterior portion of the opposite surface of the anterior peel strip via the anterior anchor and where a first posterior portion of the opposite surface of the posterior peel strip is attached to a second posterior portion of the opposite surface of the posterior peel strip via the posterior anchor.

In another aspect, the present invention provides an absorbent article defining a body-facing surface and a garment facing surface. The absorbent article includes at least one anterior attachment region or posterior attachment region. The anterior attachment region includes an anterior body adhesive disposed on the body-facing surface, an anterior peel strip overlaying the anterior body adhesive, and an anterior lateral fold. The anterior peel strip defines a body adhesive facing surface and an opposite surface. The opposite surface includes an anterior anchor. A first anterior portion of the anterior peel strip is attached to a second anterior portion of the opposite surface of the anterior peel strip via the anterior anchor. The posterior attachment region includes a posterior body adhesive disposed on the body-facing surface, a posterior peel strip overlaying the posterior body adhesive, and a posterior lateral fold. The posterior peel strip defines a body adhesive facing surface and an opposite surface. The opposite surface includes a posterior anchor. A first posterior portion of the anterior peel strip is attached to a second posterior portion of the opposite surface of the posterior peel strip via the posterior anchor. In some embodiments, the absorbent article may include a shell and an absorbent component. The shell defines, in a longitudinal direction, the anterior attachment region, an anterior separation zone, an absorbent component region, a posterior separation zone, and the posterior attachment region. The anterior separation zone separates the anterior attachment region from the absorbent component region and the posterior separation zone separates the posterior attachment region from the absorbent component region. In various embodiments, at least one of the anterior separation zone and the posterior separation zone is devoid of absorbent material and body adhesive.

In various embodiments, the absorbent article includes both the anterior attachment region and the posterior attachment region.

In another aspect, the present invention provides a method for donning an absorbent article. The method includes exposing a first posterior portion of a posterior body adhesive; grasping a second posterior portion of a posterior peel strip at a location covering a second posterior portion of the posterior body adhesive; and attaching the first posterior portion of the posterior body adhesive to a posterior part of the body. The method also includes exposing the second posterior portion of the posterior body adhesive and attaching the second posterior portion of the posterior body adhesive to the posterior part of the body. The method further includes exposing a first anterior portion of an anterior body adhesive; grasping a second anterior portion of an anterior peel strip at a location covering a second anterior portion of the anterior body adhesive; and attaching the first anterior portion of the anterior body adhesive to an anterior part of the body. The method also includes exposing the second anterior portion of the anterior body adhesive and attaching the second anterior portion of the anterior body adhesive area to the anterior part of the body.

In various embodiments, the step of exposing a first posterior portion of the posterior body adhesive includes grasping a posterior finger tab extending from the posterior peel strip and moving the posterior finger tab from a first position to a second position to define a posterior doubled region folded along a posterior peel strip hinge. Additionally, the step of grasping a second posterior portion of the posterior peel strip includes grasping the posterior doubled region. The step of exposing the second posterior portion of the posterior body adhesive includes grasping the posterior finger tab in the second position and peeling the posterior doubled region to remove the posterior peel strip. The step of exposing a first anterior portion of the anterior body adhesive includes grasping an anterior finger tab extending from the anterior peel strip and moving the anterior finger tab from a first position to a second position to define an anterior doubled region folded along an anterior peel strip hinge. The step of grasping a second anterior portion of the anterior peel strip includes grasping the doubled region. The step of exposing the second anterior portion of the anterior body adhesive includes grasping the anterior finger tab in the second position and peeling the doubled region to remove the anterior peel strip.

In various embodiments, the step of exposing the first posterior portion of the posterior body adhesive includes grasping a first posterior finger tab from a first posterior peel strip and removing the first posterior peel strip. The step of exposing the second portion of the posterior body adhesive includes grasping a second posterior finger tab from a second posterior peel strip and removing the second posterior peel strip. The step of exposing the first portion of the anterior body adhesive includes grasping a first anterior finger tab from a first anterior peel strip and removing the first anterior peel strip. The step of exposing the second portion of the anterior body adhesive includes grasping a second anterior finger tab from a second anterior peel strip and removing the second anterior peel strip.

In some embodiments, the step of exposing the first posterior portion of the posterior body adhesive and the first anterior portion of the anterior body adhesive includes unfolding the absorbent article along a longitudinal fold to define a posterior doubled region of the posterior peel strip and an anterior doubled region of the anterior peel strip. The step of grasping a second posterior portion of the posterior peel strip includes grasping the posterior doubled region. The step of grasping a second anterior portion of the anterior peel strip includes grasping the anterior doubled region. The step of exposing the second posterior portion of the posterior body adhesive includes peeling the posterior doubled region to remove the posterior peel strip. The step of exposing the second anterior portion of the anterior body adhesive includes peeling the anterior doubled region to remove the anterior peel strip.

In various embodiments, the step of exposing the first posterior portion of the posterior body adhesive includes unfolding the absorbent article along a posterior lateral fold and the step of exposing the first anterior portion of the anterior body adhesive includes unfolding the absorbent article along an anterior lateral fold.

BRIEF DESCRIPTION OF THE DRAWINGS

FIG. 3C representatively illustrates a top plan view of the absorbent article of FIG. 3A with the posterior attachment region in an exposed condition and the anterior attachment region in a fixed donning condition.

FIG. 3D representatively illustrates a top plan view of the absorbent article of FIG. 3A with both the posterior attachment region and the anterior attachment region in an exposed condition.

FIG. 4C representatively illustrates a top plan view of the absorbent article of FIG. 4A with the posterior attachment region in an exposed condition and the anterior attachment region in a fixed donning condition.

FIG. 4D representatively illustrates a top plan view of the absorbent article of FIG. 4A with both the posterior attachment region and the anterior attachment region in an exposed condition.

FIG. 5C representatively illustrates a top plan view of the absorbent article of FIG. 5A with the posterior attachment region in an exposed condition and the anterior attachment region in a fixed donning condition.

FIG. 5D representatively illustrates a top plan view of the absorbent article of FIG. 5A with both the posterior attachment region and the anterior attachment region in an exposed condition.

FIG. 6C representatively illustrates a top plan view of the absorbent article of FIG. 6A with the posterior attachment region in an exposed condition and the anterior attachment region in a fixed donning condition.

FIG. 6D representatively illustrates a top plan view of the absorbent article of FIG. 6A with both the posterior attachment region and the anterior attachment region in an exposed condition.

DETAILED DESCRIPTION OF THE DRAWINGS

The present invention provides a body-adhering product and method for donning the product that assists the user in properly positioning the product on the body while reducing the likelihood of body adhesive fouling. Specifically, the present invention provides a body-adhering feminine hygiene product and method for donning the product that assists the user in properly positioning the product in the perineum to absorb menses, urine, and other body exudates while reducing the likelihood of body adhesive fouling.

Figure 1:
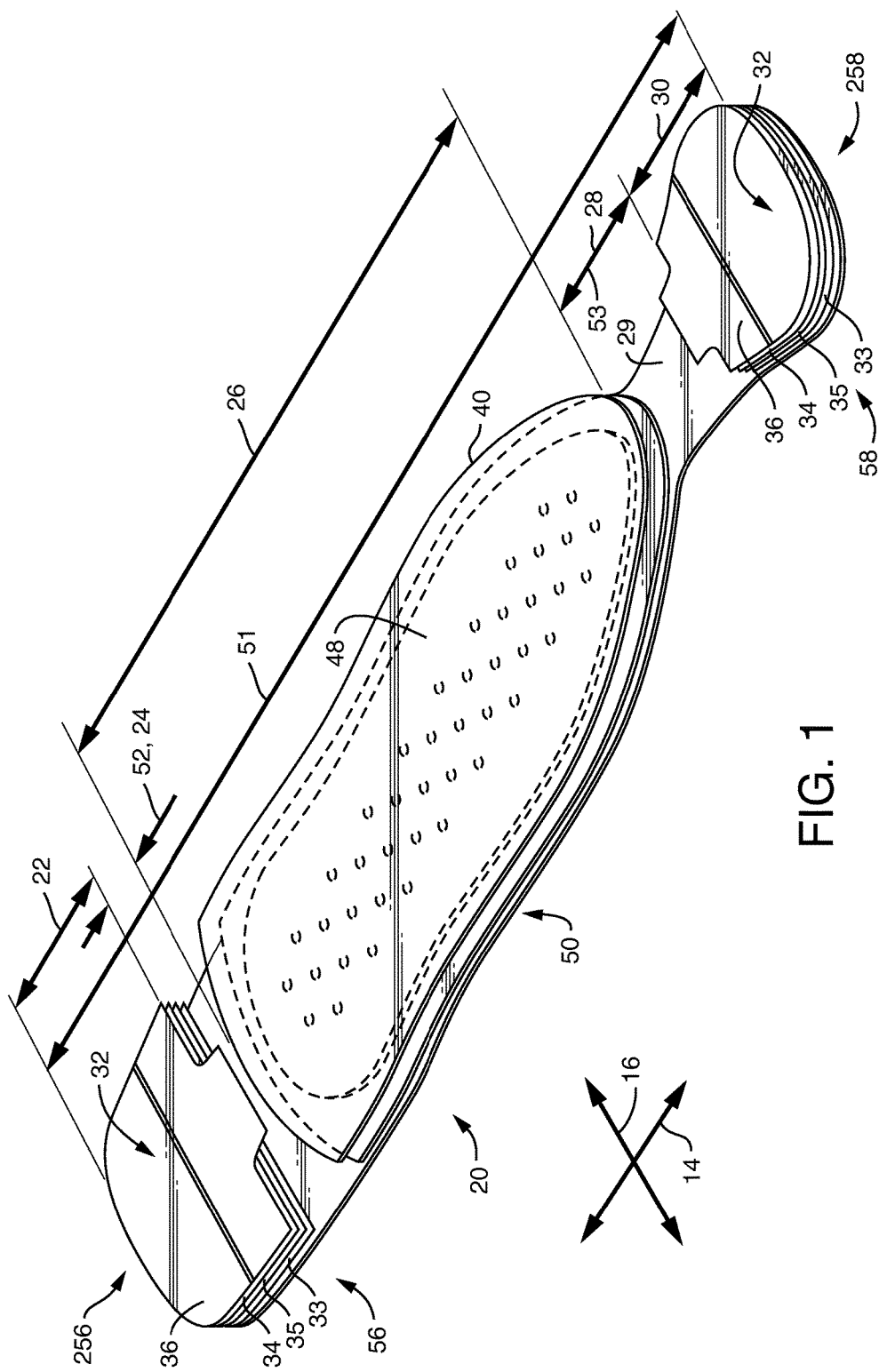
FIG. 1 representatively illustrates a top perspective view of an exemplary absorbent article of the present invention.
Figure 2:
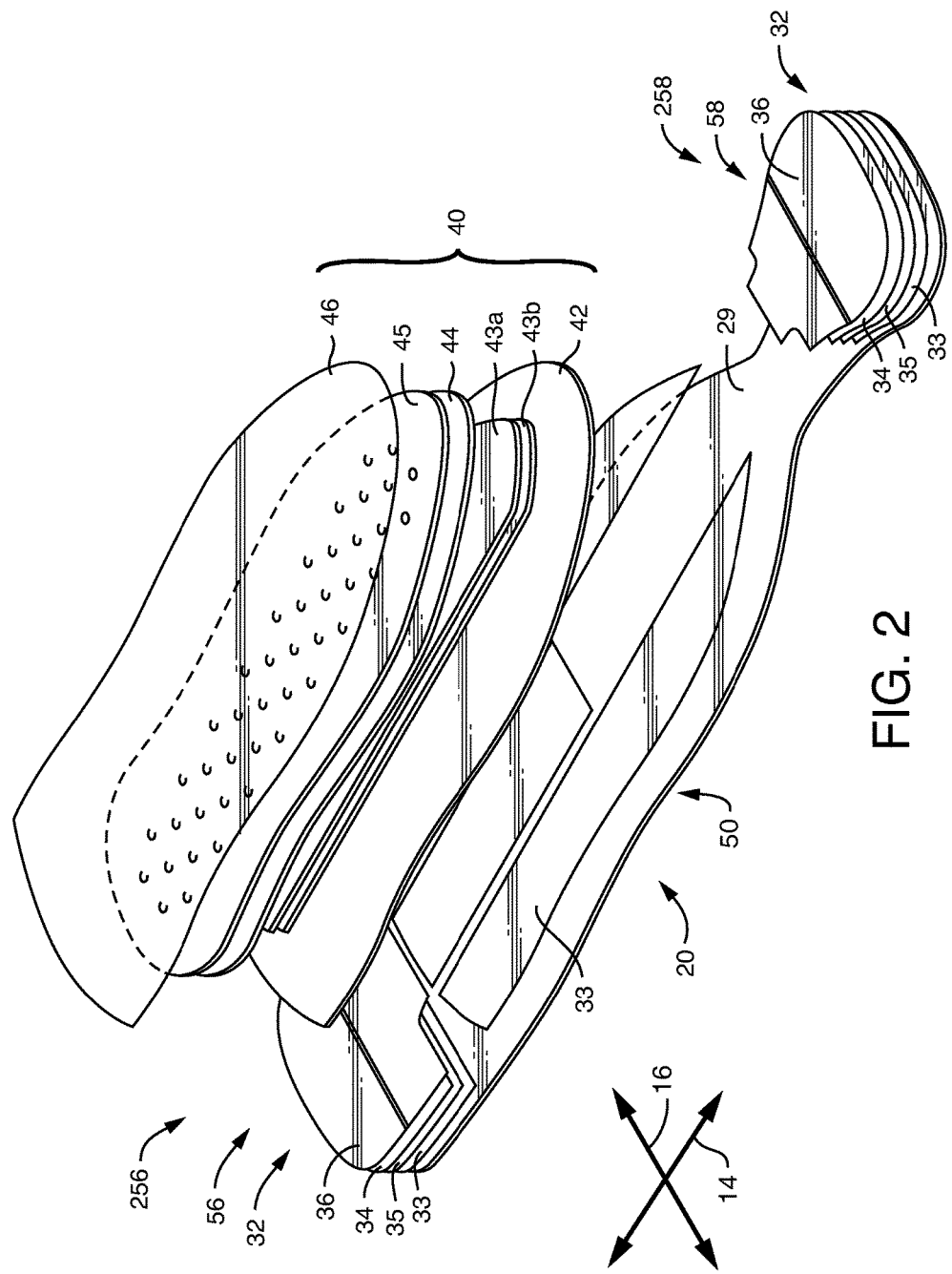
FIG. 2 representatively illustrates an exploded view of the absorbent article of FIG. 1.

Now with reference to FIGS. 1 and 2, one embodiment of a body-adhering absorbent article 20 is illustrated. FIG. 1 is a top perspective view of body-adhering absorbent article 20. FIG. 2 illustrates an exploded view of the body-adhering absorbent article 20 of FIG. 1 to better illustrate optional underlying elements. The absorbent article 20 defines a longitudinal direction 14 and a lateral direction 16 perpendicular thereto. The absorbent article 20 further defines an anterior attachment region 22, an anterior separation zone 24, an absorbent component region 26, a posterior separation zone 28, and a posterior attachment region 30. The absorbent article 20 includes a body-facing surface 48 and a garment-facing surface 50. The absorbent article 20 also includes an anterior donning system 256 and a posterior donning system 258.

As used herein, "body-facing surface" means that surface of the absorbent article which is intended to be disposed toward or placed adjacent to the body of the wearer during ordinary use. The "garment-facing surface" is on the opposite side of the absorbent article from the body-facing surface. The garment-facing surface is an outward surface of the absorbent article and is intended to be disposed to face away from the wearer's body during ordinary use. The garment-facing surface is generally arranged to face toward or placed adjacent to the wearer's undergarments when the absorbent article is worn.

Body-adhering absorbent article 20 includes a shell 29 and an absorbent component 40. The shell 29 further includes any suitable body adhesive 34. The body adhesive 34 may be applied to shell 29 at any suitable location via any suitable means. In some embodiments, the body adhesive 34 may be incorporated as part of an adhesive transfer layer 32. The adhesive transfer layer 32 may include any suitable configuration. For example, the adhesive transfer layer 32 may consist of construction adhesive 33, body adhesive 34, nonwoven carrier 35, and one or more peel strips 36.

In addition to the shell 29 and the adhesive transfer layer 32, the body adhering absorbent article 20 also includes an absorbent component 40, which is generally attached to the body-facing surface 48 of the shell 29. The attachment may be in a permanent manner, meaning that the absorbent component 40 is generally intended not to be removable by the wearer of the article 20. Alternatively, the absorbent component 40 may be constructed to be removable by the wearer, meaning that the absorbent component 40 may be removed and replaced with another absorbent component 40 by the wearer of the article 20, or be replaced with nothing at all. In some aspects, when the absorbent component 40 is attached to the shell 29 in a permanent manner, meaning that the absorbent component 40 is not intended to be removed by the wearer, various bonding means can be used, such as a construction adhesive for example. Examples of useable construction adhesives include any adhesive which will effectively hold the absorbent component 40 in place, so as not to be separated from the shell 29. Commercially available construction adhesives usable in the present invention include, for example, Rextac™ adhesives available from Huntsman Polymers, Houston, Tex. Other means may be used to hold the absorbent component 40 to the shell 29 including bonding techniques known in the art, including, but not limited to, adhesive bonds, cohesive bonds, thermal bonds, ultrasonic bonds, embossing, crimping, entangling, fusing, hook and loop, or the like, and combinations thereof.

Where the absorbent component 40 is preferably removably attached, the absorbent component 40 is held in place on the shell 29 by a means which will allow the wearer to remove the absorbent component 40. One such means of holding the absorbent component 40 is by using a pressure sensitive adhesive. Suitable pressure sensitive adhesives include, but are not limited to, any commercially available pressure sensitive adhesive. Examples of suitable pressure sensitive adhesives usable to removably hold the absorbent article 40 in place on the shell 29 include pressure sensitive adhesives available from National Starch, Bridgewater, N.J.

In certain embodiments it may be advantageous for the absorbent component 40 to have a backsheet 42 and more preferably a fluid impervious backsheet. The backsheet can serve to provide liquid impermeability for the absorbent component 40, such that any fluids entering the absorbent component 40 will not flow through the structure to the clothing of a wearer. One example of a commercially available fluid impervious backsheet is the XP-3473a baffle available from Huntsman Packaging Corporation, Houston, Tex.

The absorbent component 40 may include one or more wicking layers. For example, the absorbent component 40 may include wicking layers 43a and 43b, which may be formed from meltblown microfiber such as the 50 gsm meltblown fibers commercially available from Yuhan-Kimberly Ltd., Korea. The absorbent component 40 may further comprise an absorbent layer 44, intake layer 45 and topsheet 46. The absorbent layer 44 may contain one or more layers of absorbent materials, such as fibrous materials and/or superabsorbent materials for example. Each of the layers can contain similar materials or different materials. Materials that can be used to form the absorbent layer 44 include those materials conventionally used in absorbent articles and includes materials, such as, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A desired material is wood pulp fluff, for it is low in cost, relatively easy to form, and has good absorbency.

Topsheet 46 should be able to manage different body excretions depending on the type of product. In feminine care products, often the body-side liner or topsheet 46 must be able to handle menses and urine. In certain embodiments the topsheet 46 may include a layer constructed of any operative material and may be a composite material. For example, the body-side liner or body-contacting layer can include a woven fabric, a nonwoven fabric, a polymer film, a film-nonwoven fabric laminate or the like, as well as combinations thereof.

The backsheet 42 may be fluid impermeable or fluid pervious. The back sheet 42 may, for example, include a polymeric film, a woven fabric, a nonwoven fabric or the like, as well as combinations or composites thereof. For example, the backsheet 42 may include a polymer film laminated to a woven or nonwoven fabric. In a particular feature, the polymer film can be composed of polyethylene, polypropylene, polyester or the like, as well as combinations thereof. Construction adhesive 33 is applied to backsheet 42 and the topsheet 46. Absorbent component 40 is sandwiched between and laminated to back sheet 42 and topsheet 46.

The shell 29 can include a polymeric film, a woven fabric, a nonwoven fabric, a foam or the like, as well as combinations or composites thereof. In some aspects, shell 29 may include a laminate structure, such as a polymer film laminated to a woven or nonwoven fabric. In some embodiments, the shell 29 may be a composite material made of two or more separate pieces of material joined together in the longitudinal direction 14 and/or the lateral direction 16 to create the whole. In an alternate embodiment, not shown, the absorbent article may include a shell that consists of 2-5 separated materials that are seamed and/or bonded together to make one continuous shell layer of the absorbent article. In other embodiments, the shell 29 may be a single whole material extending in the longitudinal direction 14 and/or the lateral direction 16.

In some embodiments, the shell 29 is corona treated to improve its adhesion properties. Alternately the shell 29 can be pre-corona treated. In some embodiments, the shell 29 may be a nonwoven web of fibrous material such as, for example, a spunbond web, a meltblown web, bonded carded web, or a combination thereof. The material may be made of an elastomeric fiber forming polymer. A meltblown web used in this invention may initially be produced using conventional meltblowing processes and apparatus as known in the art whereby a cohesive web is formed. A nonwoven composite web used in this invention may initially be formed by techniques also well known in the art and described in U.S. Publication No. 2008/0095978. The composition of the body adhering shell 29 may be a stretchable laminate of a woven or nonwoven fabric with a silicone polymer, wherein the silicone polymer has adhesive properties. In this aspect, the garment-facing surface of the shell can be the woven or nonwoven fabric and the body-facing surface of the shell can include the silicone polymer. Other suitable materials and methods of manufacturing the body-adhering absorbent articles of the present invention are disclosed in U.S. patent application Ser. No. 13/022,706 and Ser. No. 13/022,700, filed on Feb. 8, 2011, the entirety of both are incorporated herein by reference where not contradictory.

In some embodiments, portions of the shell 29 may be deadened. Deadening refers to the process by which the extension, retraction or elastic properties of a web are reduced or eliminated by, for example, bonding, the application of heat, adhesive or a patch of inelastic material, or combinations thereof. Bonding means may include, but are not limited to pressure bonding, ultrasonic bonding, adhesive bonding, thermal bonding, or the like. In some embodiments, various regions are deadened by forming bond lines in one or more selected regions of the stretchable nonwoven web or laminate material in one or more selected directions, whereby the stretchability in the selected direction of the material can be controlled and substantially reduced in the region(s) of the bond lines.

In some embodiments, components such as an adhesive transfer layer 32 or an absorbent component 40 are attached to the deadened regions of the shell 29. The components may be attached using any method known in the art, for example, pressure bonding, adhesive bonding, thermal bonding and ultrasonic welding.

In some embodiments, the anterior separation zone 24 and/or the posterior separation zone 28 may be devoid of absorbent material and/or may be devoid of body adhesive. Referring now to FIG. 1, the shell 29 defines a shell length 51, the anterior separation zone 24 defines an anterior separation zone length 52 and the posterior separation zone 28 defines a posterior separation zone length 53. In various embodiments, the shell length 51 may be 300 to 400 mm, 330 to 350 mm, or about 340 mm. In some embodiments, the shell length 51 may be at least 250, at least 275, at least 300, at least 325, at least 350, or at least 375 mm. In various embodiments, the anterior separation zone length 52 may be 1 to 30 mm, 5 to 20 mm, 10 to 15 mm, or about 11 mm. In some embodiments, the anterior separation zone length 52 may be at least 5 or at least 10 mm. In various embodiments, the posterior separation zone length 53 may be 10 to 100 mm, 20 to 75 mm, 30 to 50 mm, or about 44 mm. In some embodiments, the posterior separation zone length 53 may be at least 10, at least 20, at least 30, or at least 40 mm.

In some embodiments, the anterior separation zone length 52 is at least 1, at least 2, or at least 3% of the shell length 51. In some embodiments, the posterior separation zone length 53 is at least 10, at least 11, or at least 12% of the shell length 51.

In various embodiments, the anterior separation zone 24 may be elastic. Additionally or alternatively, in various embodiments, the posterior separation zone 28 may be elastic. In various embodiments, the anterior attachment region 22 and/or the posterior attachment region 30 may be inelastic.

Referring now to FIGS. 3A, 4A, 5A, 6A, 7A, and 8A, the anterior attachment region 22 includes an anterior body adhesive and an anterior donning system illustrated in a protected condition 64. In the protected condition 64, the anterior body adhesive is fully covered by one or more anterior peel strips. When the user is ready to apply the body adhering article, the anterior attachment region 22 is adapted to transition from the protected condition 64 to a fixed donning condition 68 as illustrated in FIGS. 3C, 4C, 5C, 6C, 7C, and 8E. As used herein, the term "fixed donning condition" refers to a specific static state of the anterior and/or posterior attachment regions wherein a portion of the body adhesive in the anterior and/or posterior attachment regions is exposed and a portion of the body adhesive in the respective attachment region is covered and the portions will remain in said condition indefinitely absent further user interaction. For example, the donning condition can be "fixed" via hinges, complete removal of material, mechanical anchoring, and the like. The term "fixed donning condition" is distinguished from a transitory condition wherein a portion of the body adhesive is exposed and a portion of the body adhesive is covered. For example, the transitory process of peeling a peel strip from a body adhesive is not a fixed donning condition as that term is used herein.

In the fixed donning condition 68, a first anterior portion of the anterior body adhesive is exposed and a second anterior portion of the anterior body adhesive is covered by the one or more anterior peel strips. The user may then grasp the covered portion without fouling the adhesive and apply the exposed first anterior portion to the body. Once complete with this step, the anterior attachment region is adapted to transition from the fixed donning condition 68 to a fully exposed condition 72 as illustrated in FIGS. 3D, 4D, 5D, 6D, 7D, and 8F. In the fully exposed condition 72, both the first anterior portion and the second anterior portion of the anterior body adhesive are fully exposed.

Likewise, the posterior attachment region 30 includes a posterior body adhesive and a posterior donning system illustrated in a protected condition 64 in FIGS. 3A, 4A, 5A, 6A, and 8B. In the protected condition 64, the posterior body adhesive is fully covered by one or more posterior peel strips. When the user is ready to apply the body adhering article, the posterior attachment region 30 is adapted to transition from the protected condition 64 to a fixed donning condition 68 as illustrated in FIGS. 3B, 4B, 5B, 6B, 7C, and 8C. In the fixed donning condition 68, a first posterior portion of the posterior body adhesive is exposed and a second portion of the posterior body adhesive is covered by the one or more posterior peel strips. The user may then grasp the covered portion without fouling the adhesive and apply the exposed first posterior portion to the body. Once complete with this step, the posterior attachment region 30 is adapted to transition from the fixed donning condition 68 to a fully exposed condition 72 as illustrated in FIGS. 3C, 4C, 5C, 6C, 7D, and 8D. In the fully exposed condition 72, both the first posterior portion and the second posterior portion of the posterior body adhesive are fully exposed.

Referring now to FIGS. 3A-8F, a method for donning an absorbent article includes exposing a first portion of a posterior body adhesive to define a fixed donning condition 68. The method further includes grasping a posterior peel strip at a location covering a second portion of the posterior body adhesive and attaching the first portion of the posterior body adhesive to a posterior part of the body. The method also includes the step of exposing the second portion of the posterior body adhesive to define a fully exposed condition 72 and attaching the second posterior portion of the posterior body adhesive to the posterior part of the body.

The method for donning an absorbent article also includes exposing a first portion of an anterior body adhesive to define a fixed donning condition 68. The method further includes grasping an anterior peel strip at a location covering a second portion of the anterior body adhesive and attaching the first portion of the anterior body adhesive to an anterior part of the body. The method also includes the step of exposing the second portion of the anterior body adhesive to define a fully exposed condition 72 and attaching the second portion of the anterior body adhesive to the anterior part of the body.

Referring now to FIGS. 3A-3D, a top plan view of an absorbent article 20 in various donning conditions is representatively illustrated. The absorbent article 20 defines a body-facing surface 48 and a garment facing surface 50 (i.e., the surface facing away from the viewer in this perspective). The absorbent article 20 includes an anterior attachment region 22 having an anterior body adhesive 62 disposed on the body-facing surface 48 and having an anterior donning system 21 with an anterior peel strip 66 overlaying the anterior body adhesive 62. Likewise, the absorbent article 20 includes a posterior attachment region 30 having a posterior body adhesive 74 disposed on the body-facing surface 48 and having a posterior donning system 23 with a posterior peel strip 76 overlaying the posterior body adhesive 74. The absorbent article 20 is illustrated with both the anterior attachment region 22 and the posterior attachment region 30 in a protected condition 64 in FIG. 3A. In other words, the anterior body adhesive 62 and the posterior body adhesive 74 are protected from fouling by the anterior peel strip 66 and the posterior peel strip 76 respectively.

Figures 3A, 3B:
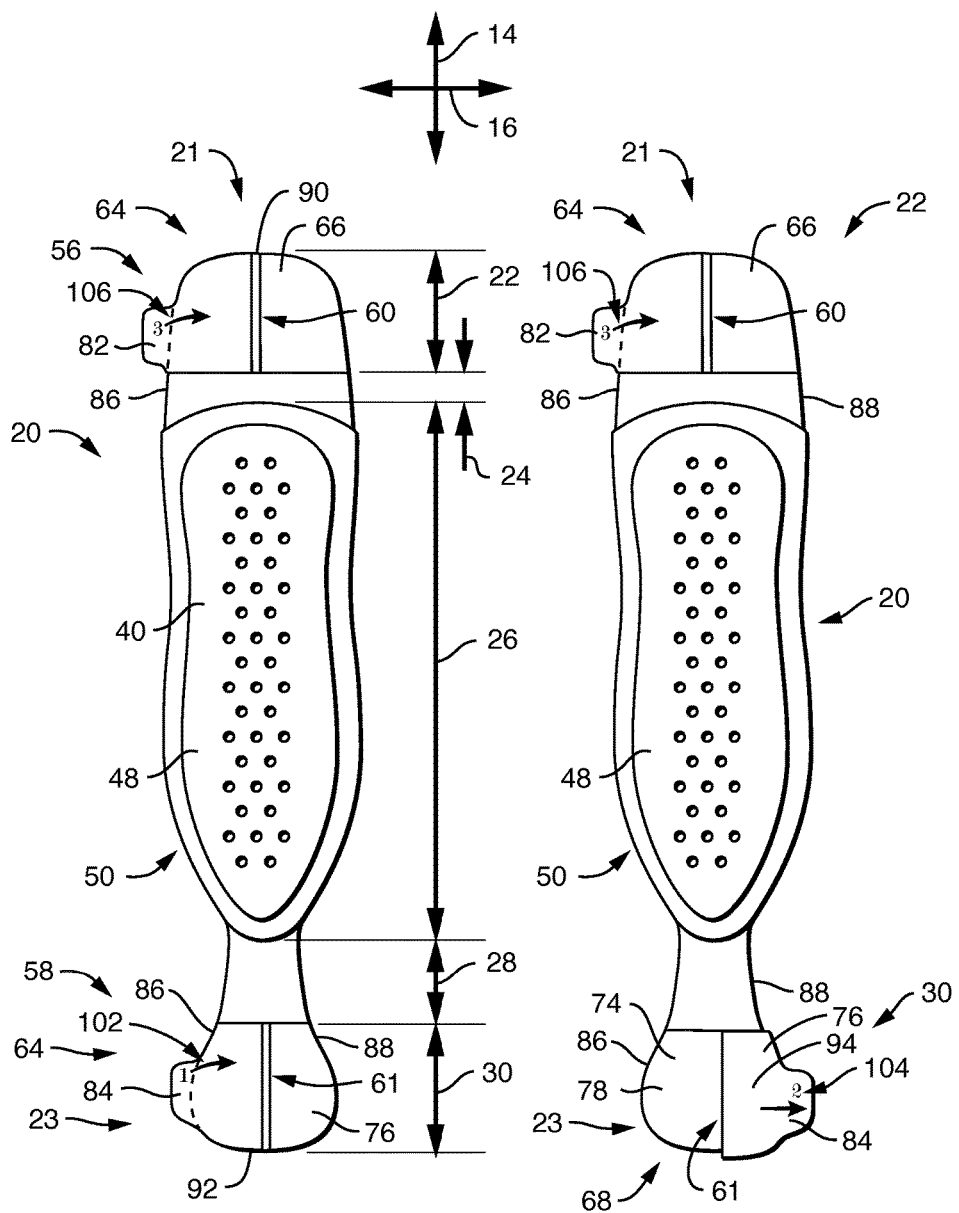
FIG. 3A representatively illustrates a top plan view of an exemplary absorbent article with both the anterior and posterior attachment regions in a protected condition.
FIG. 3B representatively illustrates a top plan view of the absorbent article of FIG. 3A with the posterior attachment region in a fixed donning condition and the anterior attachment region in a protected condition.

In various embodiments, at least one of the anterior peel strips and the posterior peel strips include a hinge generally oriented in the longitudinal direction. For example, as illustrated in FIG. 3A, both the anterior peel strip 66 and the posterior peel strip 76 include a hinge. Specifically, the anterior peel strip 66 includes an anterior hinge 60 and the posterior peel strip 76 includes a posterior hinge 61. As used herein, the term "hinge" refers to a line of weakness mechanically created during the manufacturing process. For example, the line of weakness can be mechanically created by scoring, perforating, thinning, melting, embossing, or otherwise manipulating the peel strip material during manufacturing to promote the preferential folding along the line of weakness during the donning process. The hinge separates two distinct areas of the peel strip wherein at least a portion of both areas overlay the body adhesive.

In various embodiments, at least one of the anterior peel strips and the posterior peel strips include a finger tab. For example, as illustrated in FIG. 3A, both the anterior peel strip 66 and the posterior peel strip 76 include a finger tab. Specifically, the anterior peel strip 66 includes an anterior finger tab 82 and the posterior peel strip 76 includes a posterior finger tab 84. The anterior finger tab 82 and/or the posterior finger tab 84 may extend beyond a first longitudinal edge 86 or a second longitudinal edge 88 of the absorbent article 20. Likewise, the anterior finger tab 82 may extend beyond a first lateral edge 90 and/or the posterior finger tab 84 may extend beyond a second lateral edge 92 of the absorbent article 20. In various embodiments, the anterior finger tab may extend beyond the area covered by the anterior body adhesive and/or the posterior finger tab may extend beyond the area covered by the posterior body adhesive. For example, as illustrated in FIG. 3A, the anterior finger tab 82 extends beyond the area covered by the anterior body adhesive 62 (FIG. 3D). Likewise, the posterior finger tab 84 extends beyond the area covered by the posterior body adhesive 74 (FIG. 3D).

In use, the anterior peel strip 66 may be adapted to fold along the anterior hinge 60 to expose a first anterior portion 70 of the anterior body adhesive 62 as illustrated in FIG. 3C. Similarly, the posterior peel strip 76 may be adapted to fold along the posterior hinge 61 to expose a first posterior portion 78 of the posterior body adhesive 74 as illustrated in FIG. 3B. When the anterior peel strip 66 is folded along the anterior hinge 60, the anterior attachment region 22 is in the fixed donning condition 68 as illustrated in FIG. 3C. When the posterior peel strip 76 is folded along the posterior hinge 61, the posterior attachment region 30 is in the fixed donning condition 68 as illustrated in FIG. 3B.

In various embodiments, the anterior finger tab 82 may extend from the first longitudinal edge 86 of the absorbent article 20 in the protected condition 64 as illustrated in FIG. 3A and the anterior finger tab 82 may extend from the second longitudinal edge 88 of the absorbent article 20 when in the fixed donning condition 68 as illustrated in FIG. 3C.

In various embodiments, the posterior finger tab 84 may extend from the first longitudinal edge 86 of the absorbent article 20 in the protected condition 64 as illustrated in FIG. 3A and the posterior finger tab 84 may extend from the second longitudinal edge 88 of the absorbent article 20 when in the fixed donning condition 68 as illustrated in FIG. 3B.

The absorbent article 20 illustrated in FIGS. 3A-3D facilitates a method for donning the absorbent article via the anterior donning system 21 and the posterior donning system 23. The method includes grasping the posterior finger tab 84 extending laterally from the posterior peel strip 76 overlaying the posterior body adhesive 74. The method further includes moving the posterior finger tab 84 in the lateral direction 16 from the first position overhanging the first longitudinal edge 86, as illustrated in FIG. 3A, to a second position overhanging the second longitudinal edge 88 as illustrated in FIG. 3B. The movement of the posterior finger tab 84 folds the posterior peel strip 76 along the posterior hinge 61. The movement of the posterior finger tab 84 also exposes the first posterior portion 78 of the posterior body adhesive 74. The folded posterior peel strip 76 now defines a doubled region 94 overlaying the second posterior portion 79 of the posterior body adhesive 74.

The method further includes the step of grasping the doubled region 94 and attaching the first posterior portion 78 of the posterior body adhesive 74 to the posterior part of the body. For example, the method may include attaching the first posterior portion 78 proximate the small of the user's back. Specifically, the method may include attaching the first posterior portion 78 to the user's body proximate the sacral triangle.

The method further includes the step of grasping the posterior finger tab 84 in the second position overhanging the second longitudinal edge 88 and peeling the posterior peel strip 76 from the posterior attachment region 30 to expose the second posterior portion 79 of the posterior body adhesive 74 as illustrated in FIG. 3C. The method further includes attaching the second posterior portion 79 of the posterior body adhesive 74 to the posterior part of the body. For example, the method may include peeling the doubled region 94 from the posterior attachment region 30 while smoothing the second posterior portion 79 onto the posterior part of the body.

The method also includes grasping the anterior finger tab 82 extending laterally from the anterior peel strip 66 overlaying the anterior body adhesive 62. The method further includes moving the anterior finger tab 82 in the lateral direction 16 from the first position overhanging the first longitudinal edge 86, as illustrated in FIG. 3A, to a second position overhanging the second longitudinal edge 88, as illustrated in FIG. 3C. The movement of the anterior finger tab 82 folds the anterior peel strip 66 along the anterior hinge 60. The movement of the anterior finger tab 82 also exposes the first anterior portion 70 of the anterior body adhesive 62. The folded anterior peel strip 66 now defines a doubled region 96 overlaying the second anterior portion 71 of the anterior body adhesive 62.

The method further includes the step of grasping the doubled region 96 and attaching the first anterior portion 70 of the anterior body adhesive 62 to the anterior part of the body. For example, the method may include attaching the first anterior portion 70 proximate the mons veneris. In some embodiments, the user may stretch and position the absorbent article 20 relative to the body before attaching the first anterior portion 70 of the anterior body adhesive 62 to the anterior part of the body. In some embodiments, the user may stretch the absorbent article 20 using the previously attached posterior body adhesive 74 to create a counter force.

The method further includes the step of grasping the anterior finger tab 82 in the second position overhanging the second longitudinal edge 88 and peeling the anterior peel strip 66 from the anterior attachment region 22 to expose the second anterior portion 71 of the anterior body adhesive 62, as illustrated in FIG. 3D. The method further includes attaching the second anterior portion 71 of the anterior body adhesive 62 to the anterior part of the body.

In various embodiments, the method may include the steps associated with the attachment of the posterior attachment region 30 before the steps associated with the attachment of the anterior attachment region 22. In other embodiments, the method may include the steps associated with the attachment of the anterior attachment region 22 before the steps associated with the attachment of the posterior attachment region 30.

In some embodiments one or more indicia may be provided on the absorbent article to guide a user in the method of use. For example, referring again to FIG. 3A, a first indicia 102 is provided on the body-facing surface 48 of the posterior peel strip 76 to signal the first step in one exemplary donning process. In this example, the first indicia 102 include the printed number "1" and a printed arrow to signal that the first step in the exemplary donning process is to move the posterior finger tab 84 in the lateral direction 16.

Referring now to FIG. 3B, a second indicia 104 is provided on the garment-facing surface 50 of the posterior peel strip 76 to signal the second step in the exemplary donning process. The second indicia 104 include the printed number "2" and a printed arrow to signal that the second step in the exemplary donning process is to grasp the posterior finger tab 84 and pull in the direction indicated by the arrow to remove the posterior peel strip 76 from the posterior attachment region 30. Additionally, a third indicia 106 is provided on the body-facing surface 48 of the anterior peel strip 66 to signal the third step in the exemplary donning process. The third indicia 106 include the printed number "3" and a printed arrow to signal that the third step in the exemplary donning process is to move the anterior finger tab 82 in the lateral direction 16.

Referring now to FIG. 3C, a fourth indicia 108 is provided on the garment-facing surface 50 of the anterior peel strip 66 to signal the fourth step in the exemplary process. The fourth indicia 108 include the printed number "4" and a printed arrow to signal that the fourth step in the exemplary donning process is to remove the anterior peel strip 66 from the anterior attachment region 22. In various embodiments, the indicia may be visual, tactile, or any other suitable indicators and combinations thereof.

Referring now to FIGS. 4A-4D, a top plan view of an absorbent article 220 in various donning conditions is representatively illustrated. The absorbent article 220 defines a body-facing surface 48 and a garment facing surface 50 (i.e., the surface facing away from the viewer in this perspective). The absorbent article 220 includes an anterior attachment region 22 having an anterior body adhesive 62 disposed on the body-facing surface 48 and an anterior donning system 256 with an anterior peel strip 266 overlaying the anterior body adhesive 62. Likewise, the absorbent article 220 includes a posterior attachment region 30 having a posterior body adhesive 74 disposed on the body-facing surface 48 and a posterior donning system 258 with a posterior peel strip 276 overlaying the posterior body adhesive 74. The absorbent article 220 is illustrated with both the anterior attachment region 22 and the posterior attachment region 30 in a protected condition 64 in FIG. 4A. In other words, the anterior body adhesive 62 and the posterior body adhesive 74 are protected from fouling by the anterior peel strip 266 and the posterior peel strip 276 respectively.

Figures 4A, 4B:
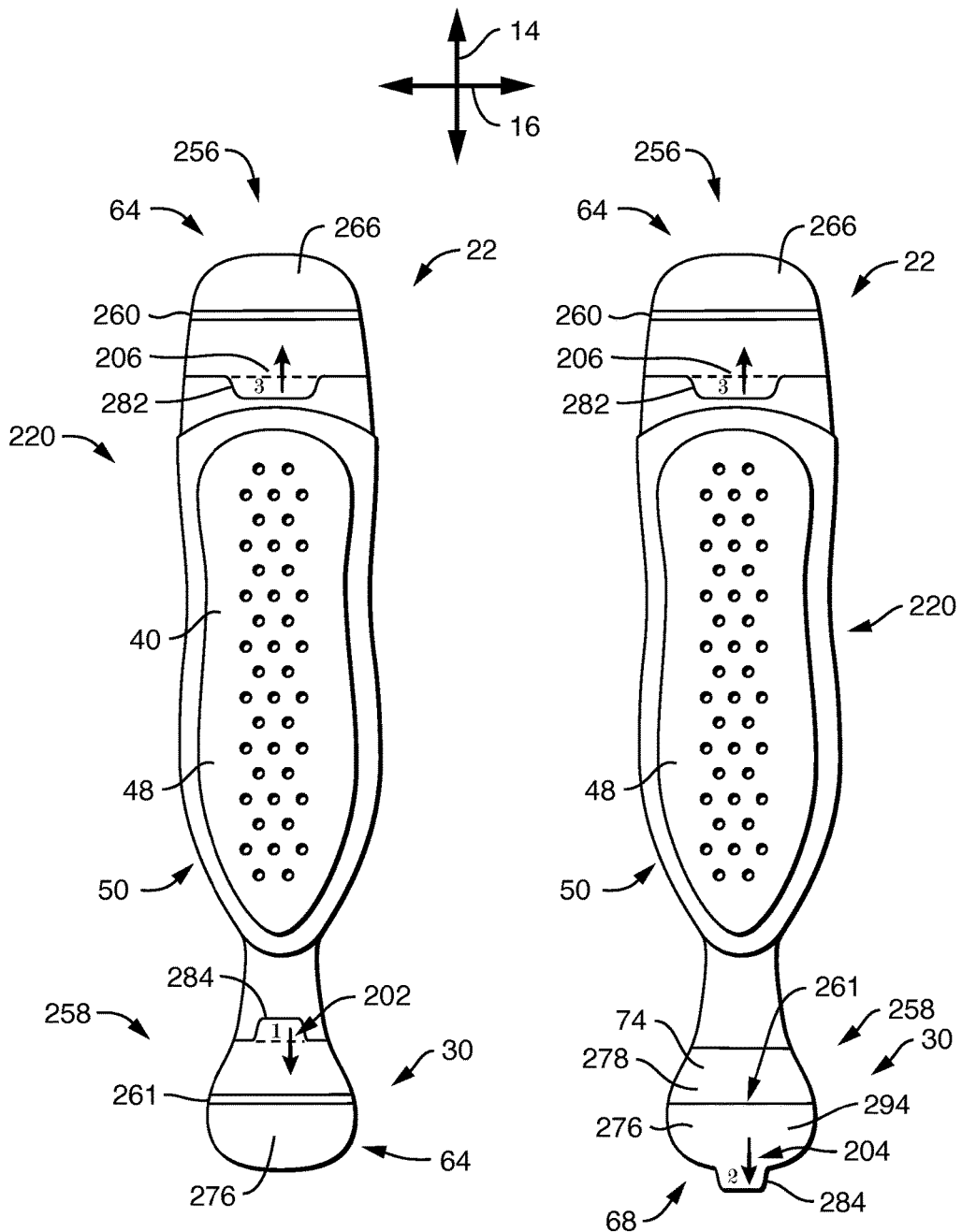
FIG. 4A representatively illustrates a top plan view of another exemplary absorbent article with both the anterior and posterior attachment regions in a protected condition.
FIG. 4B representatively illustrates a top plan view of the absorbent article of FIG. 4A with the posterior attachment region in a fixed donning condition and the anterior attachment region in the protected condition.

In various embodiments, at least one of the anterior peel strip and the posterior peel strip include a hinge generally oriented in the lateral direction. For example, as illustrated in FIG. 4A, both the anterior peel strip 266 and the posterior peel strip 276 include a hinge. Specifically, the anterior peel strip 266 includes an anterior hinge 260 and the posterior peel strip 276 includes a posterior hinge 261.

In various embodiments, at least one of the anterior peel strip and the posterior peel strip include a finger tab. For example, as illustrated in FIG. 4A, both the anterior peel strip 266 and the posterior peel strip 276 include a finger tab. Specifically, the anterior peel strip 266 includes an anterior finger tab 282 and the posterior peel strip 276 includes a posterior finger tab 284. The anterior finger tab 282 may extend beyond the area covered by the anterior body adhesive and/or the posterior finger tab 284 may extend beyond the area covered by the posterior body adhesive.

In use, the anterior peel strip 266 may be adapted to fold along the anterior hinge 260 to expose a first anterior portion 270 of the anterior body adhesive 62 as illustrated in FIG. 4C. Similarly, the posterior peel strip 276 may be adapted to fold along the posterior hinge 261 to expose a first posterior portion 278 of the posterior body adhesive 74 as illustrated in FIG. 4B. When the anterior peel strip 266 is folded along the anterior hinge 260, the anterior attachment region 22 is in the fixed donning condition 68 as illustrated in FIG. 4C. When the posterior peel strip 276 is folded along the posterior hinge 261, the posterior attachment region 30 is in the fixed donning condition 68 as illustrated in FIG. 4B.

The absorbent article 220 illustrated in FIGS. 4A-4D facilitates a method for donning the absorbent article via the anterior donning system 256 and the posterior donning system 258. The method includes grasping the posterior finger tab 284 extending from the posterior peel strip 276 overlaying the posterior body adhesive 74. The method further includes moving the posterior finger tab 284 in the longitudinal direction 14 from a first position, as illustrated in FIG. 4A, to a second position, as illustrated in FIG. 4B. The movement of the posterior finger tab 284 folds the posterior peel strip 276 along the posterior hinge 261. The movement of the posterior finger tab 284 also exposes the first posterior portion 278 of the posterior body adhesive 74. The folded posterior peel strip 276 now defines a doubled region 294 overlaying the second posterior portion 279 of the posterior body adhesive 74.

The method further includes the step of grasping the doubled region 294 and attaching the first posterior portion 278 of the posterior body adhesive 74 to the posterior part of the body. The method further includes the step of grasping the posterior finger tab 284 in the second position and peeling the posterior peel strip 276 from the posterior attachment region 30 to expose the second posterior portion 279 of the posterior body adhesive 74. The method further includes attaching the second posterior portion 279 of the posterior body adhesive 74 to the posterior part of the body. For example, the method may include peeling the doubled region 294 from the posterior attachment region 30 while smoothing the second posterior portion 279 onto the posterior part of the body.

The method also includes grasping the anterior finger tab 282 extending from the anterior peel strip 266 overlaying the anterior body adhesive 62. The method further includes moving the anterior finger tab 282 in the longitudinal direction 14 from a first position, as illustrated in FIG. 4B, to a second position, as illustrated in FIG. 4C. The movement of the anterior finger tab 282 folds the anterior peel strip 266 along the anterior hinge 260. The movement of the anterior finger tab 282 also exposes the first anterior portion 270 of the anterior body adhesive 62. The folded anterior peel strip 266 now defines a doubled region 296 overlaying the second anterior portion 271 of the anterior body adhesive 62.

The method further includes the step of grasping the doubled region 296 and attaching the first anterior portion 270 of the anterior body adhesive 62 to the anterior part of the body. In some embodiments, the user may stretch and position the absorbent article 220 relative to the body before attaching the first anterior portion 270 of the anterior body adhesive 62 to the anterior part of the body. In some embodiments, the user may stretch the absorbent article 220 using the previously attached posterior body adhesive 74 to create a counter force.

The method further includes the step of grasping the anterior finger tab 282 in the second position and peeling the anterior peel strip 266 from the anterior attachment region 22 to expose the second anterior portion 271 of the anterior body adhesive 62, as illustrated in FIG. 4D. The method further includes attaching the second anterior portion 271 of the anterior body adhesive 62 to the anterior part of the body.

In various embodiments, the method may include the steps associated with the attachment of the posterior attachment region 30 before the steps associated with the attachment of the anterior attachment region 22. In other embodiments, the method may include the steps associated with the attachment of the anterior attachment region 22 before the steps associated with the attachment of the posterior attachment region 30.

In some embodiments one or more indicia may be provided on the absorbent article to guide a user in the method of use. For example, referring again to FIG. 4A, a first indicia 202 is provided on the body-facing surface 48 of the posterior peel strip 276 to signal the first step in one exemplary donning process. In this example, the first indicia 202 include the printed number "1" and a printed arrow to signal that the first step in the exemplary donning process is to move the posterior finger tab 284 in the longitudinal direction 14.

Referring now to FIG. 4B, a second indicia 204 is provided on the garment-facing surface 50 of the posterior peel strip 276 to signal the second step in the exemplary donning process. The second indicia 204 include the printed number "2" and a printed arrow to signal that the second step in the exemplary donning process to grasp the posterior finger tab 284 and pull in the direction indicated by the arrow to remove the posterior peel strip 276 from the posterior attachment region 30. Additionally, a third indicia 206 is provided on the body-facing surface 48 of the anterior peel strip 266 to signal the third step in the exemplary donning process. The third indicia 206 include the printed number "3" and a printed arrow to signal that the third step in the exemplary donning process is to move the anterior finger tab 282 in the longitudinal direction 14.

Referring now to FIG. 4C, a fourth indicia 208 is provided on the garment-facing surface 50 of the anterior peel strip 266 to signal the fourth step in the exemplary process. The fourth indicia 208 include the printed number "4" and a printed arrow to signal that the fourth step in the exemplary donning process is to remove the anterior peel strip 266 from the anterior attachment region 22. In various embodiments, the indicia may be visual, tactile, or any other suitable indicators and combinations thereof.

Figure 5A:
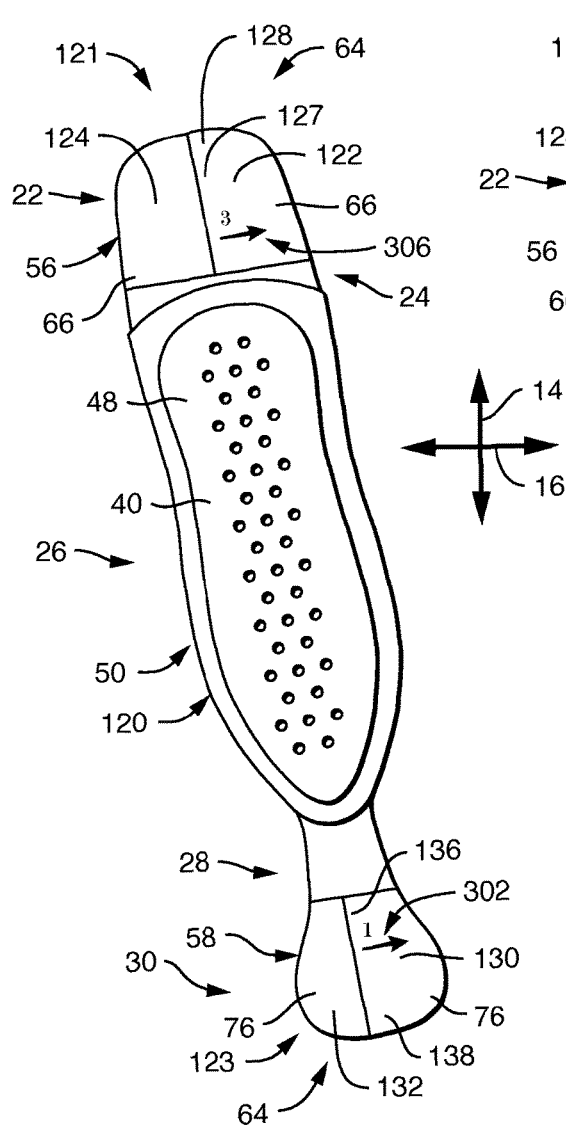
FIG. 5A representatively illustrates a top plan view of another exemplary absorbent article with both the anterior attachment region and the posterior attachment region in a protected condition.

Referring now to FIGS. 5A-5D, a top plan view of another exemplary absorbent article 120 in various donning conditions is representatively illustrated. The absorbent article 120 defines a body-facing surface 48 and a garment facing surface 50 (facing away from the viewer in this perspective). The absorbent article 120 includes an anterior attachment region 22 having an anterior body adhesive 62 disposed on the body-facing surface 48. The anterior attachment region 22 also includes an anterior donning system 121 with a first anterior peel strip 122 overlaying a first anterior portion 70 of the anterior body adhesive 62 and a second anterior peel strip 124 overlaying a second anterior portion 71 of the anterior body adhesive 62. Additionally, the anterior attachment region 22 includes an anterior adhesive-free portion 126 that is substantially free of body adhesive. In some embodiments, the anterior adhesive-free portion 126 that is substantially free of body adhesive may completely separate the first anterior portion 70 from the second anterior portion 71 as illustrated in FIG. 5D. In some embodiments, the first anterior peel strip 122 only overlaps first anterior portion 70 and a portion of the anterior adhesive-free portion 126. In these embodiments, the part of the first anterior peel strip 122 that overlaps the anterior adhesive-free portion 126 defines a first anterior finger tab 127. Likewise, in some embodiments, the second anterior peel strip 124 only overlaps the second anterior portion 71 and part of the anterior adhesive-free portion 126. In these embodiments, the part of the second anterior peel strip 124 that overlaps the anterior adhesive-free portion 126 defines a second anterior finger tab 129. In some embodiments, the first anterior peel strip 122 overlaps the second anterior peel strip 124 to define an anterior overlap region 128. In some embodiments, the second anterior peel strip overlaps the first anterior peel strip to define the anterior overlap region (not shown). In various embodiments, at least a part of the anterior overlap region 128 overlays at least a part of the anterior adhesive-free portion 126. In some embodiments, the anterior overlap region 128 may completely overlay the anterior adhesive-free portion 126.

The absorbent article 120 includes a posterior attachment region 30 having a posterior body adhesive 74 disposed on the body-facing surface 48. The posterior attachment region 30 also includes a posterior donning system 123 with a first posterior peel strip 130 overlaying a first posterior portion 78 of the posterior body adhesive 74 and a second posterior peel strip 132 overlaying a second posterior portion 79 of the posterior body adhesive 74. Additionally, the posterior attachment region 30 includes a posterior adhesive-free portion 134 that is substantially free of body adhesive. In some embodiments, the posterior adhesive-free portion 134 that is substantially free of body adhesive may completely separate the first posterior portion 78 from the second posterior portion 79 as illustrated in FIG. 5D. In some embodiments, the first posterior peel strip 130 overlaps the posterior adhesive-free portion 134. The part of the first posterior peel strip 130 that overlaps the posterior adhesive-free portion 134 defines a first posterior finger tab 138. Likewise, in some embodiments, the second posterior peel strip 132 overlaps the posterior adhesive-free portion 134. The part of the second posterior peel strip 132 that overlaps the posterior adhesive-free portion 134 defines a second posterior finger tab 140. In some embodiments, the first posterior peel strip 130 overlaps the second posterior peel strip 132 to define a posterior overlap region 136. In some embodiments, the second posterior peel strip overlaps the first posterior peel strip to define a posterior overlap region (not shown). In various embodiments, at least a part of the posterior overlap region 136 overlays at least a part of the posterior adhesive-free portion 134. In some embodiments, the posterior overlap region 136 may completely overlay the posterior adhesive-free portion 134.

Figure 5B:
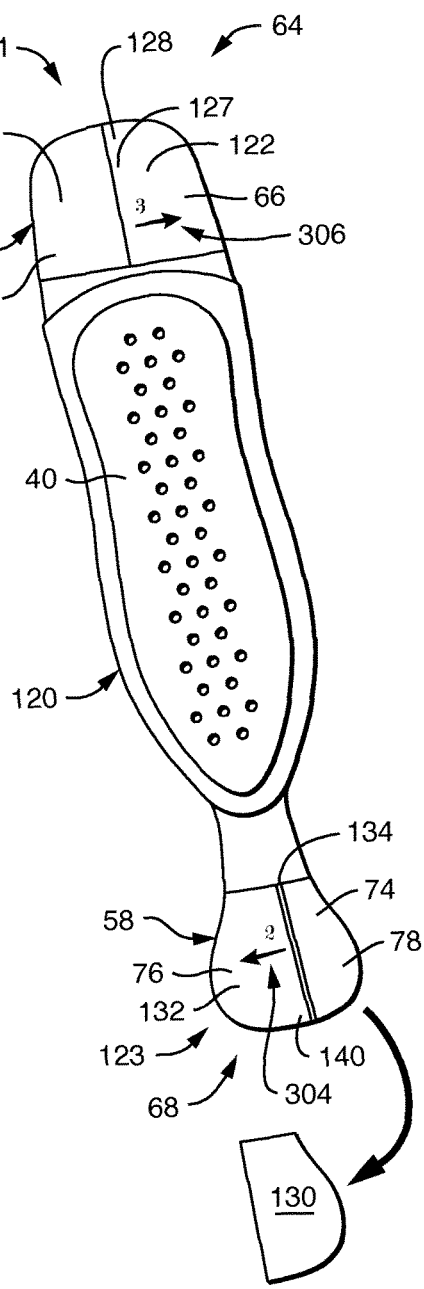
FIG. 5B representatively illustrates a top plan view of the absorbent article of FIG. 5A with the posterior attachment region in a fixed donning condition and the anterior attachment region in the protected condition.

The absorbent article 120 of FIGS. 5A-5D facilitates a method for donning an absorbent article via the anterior donning system 121 and the posterior donning system 123. The method includes grasping the first posterior finger tab 138 from the first posterior peel strip 130 overlaying the first posterior portion 78 of the posterior body adhesive 74. For example, the user may grasp the first posterior finger tab 138 between the thumb and forefinger. The method further includes removing the first posterior peel strip 130 to expose the first posterior portion 78 of the posterior body adhesive 74 as illustrated in FIG. 5B. For example, the user may remove the first posterior peel strip 130 by peeling in the lateral direction 16. The method further includes attaching the exposed first posterior portion 78 to the posterior part of the body. To attach the first posterior portion 78 to the posterior part of the body without contaminating the adhesive, the user may grasp the area covered by the second posterior peel strip 132 between the thumb and forefinger.

The method further includes the step of grasping the second posterior finger tab 140 from the second posterior peel strip 132 overlaying the second posterior portion 79 of the posterior body adhesive 74 and removing the second posterior peel strip 132 to expose the second posterior portion 79 as illustrated in FIG. 5C. The method then includes attaching the exposed second posterior portion 79 to the posterior part of the body. In some embodiments, the user may peel the second posterior peel strip 132 in the lateral direction 16 while smoothing and attaching the second posterior portion 79 to the body at the same time.

The method also includes grasping the first anterior finger tab 127 from the first anterior peel strip 122 overlaying the first anterior portion 70 of the anterior body adhesive 62 and removing the first anterior peel strip 122 to expose the first anterior portion 70 as illustrated in FIG. 5C. For example, the user may grasp the first anterior finger tab 127 between the thumb and forefinger and remove the first anterior peel strip 122 by peeling it off in the lateral direction 16 thereby exposing the first anterior portion 70 of the anterior body adhesive 62.

The method also includes attaching the exposed first anterior portion 70 of the anterior body adhesive 62 to the anterior part of the body. To attach the first anterior portion 70 to the anterior part of the body without contaminating the adhesive, the user may grasp the area covered by the second anterior peel strip 124 between the thumb and forefinger. In some embodiments, the method may further include stretching the absorbent article before attaching the exposed first anterior portion 70 to the anterior part of the body. Once the first anterior portion 70 is attached, the method also includes grasping the second anterior finger tab 129 from the second anterior peel strip 124 overlaying the second anterior portion 71 of the anterior body adhesive 62 and removing the second anterior peel strip 124 to expose the second anterior portion 71 as illustrated in FIG. 5D. Finally, the method includes the step of attaching the exposed second anterior portion 71 of the anterior body adhesive 62 to the anterior part of the body. In some embodiments, the user may peel the second anterior peel strip 124 in the lateral direction 16 while smoothing and attaching the second anterior portion 71 to the body at the same time.

In some embodiments one or more indicia may be provided on the absorbent article to guide a user in the method of use. For example, referring again to FIG. 5A, a first indicia 302 is provided on the body-facing surface 48 of the first posterior peel strip 130 to signal the first step in one exemplary donning process. In this example, the first indicia 302 include the printed number "1" and a printed arrow to signal that the first step in the exemplary donning process is to peel the first posterior peel strip 130 in the lateral direction 16.

Referring now to FIG. 5B, a second indicia 304 is provided on the body-facing surface 48 of the second posterior peel strip 132 to signal the second step in the exemplary donning process. The second indicia 304 include the printed number "2" and a printed arrow to signal that the second step in the exemplary donning process is to peel in the direction indicated by the arrow to remove the second posterior peel strip 132 from the posterior attachment region 30. Additionally, a third indicia 306 is provided on the body-facing surface 48 of the first anterior peel strip 122 to signal the third step in the exemplary donning process. The third indicia 306 includes the printed number "3" and a printed arrow to signal that the third step in the exemplary donning process is to remove the first anterior peel strip 122 by peeling in the lateral direction 16.

Referring now to FIG. 5C, a fourth indicia 308 is provided on the body-facing surface 48 of the second anterior peel strip 124 to signal the fourth step in the exemplary process. The fourth indicia 308 include the printed number "4" and a printed arrow to signal that the fourth step in the exemplary donning process is to remove the second anterior peel strip 124 from the anterior attachment region 22. In various embodiments, the indicia may be visual, tactile, or any other suitable indicators and combinations thereof.

Figures 6A, 6B:
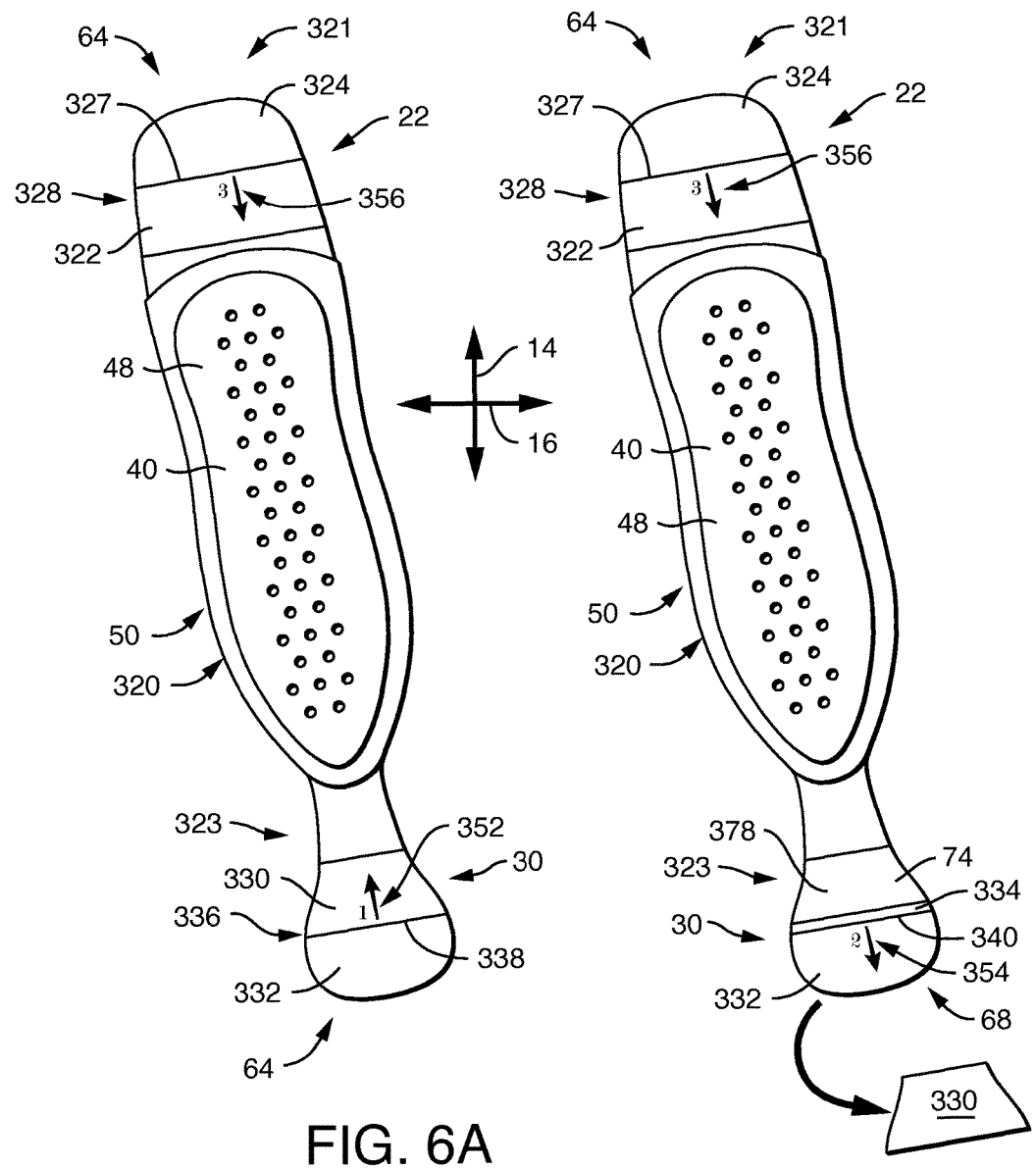
FIG. 6A representatively illustrates a top plan view of another exemplary absorbent article with both the anterior attachment region and the posterior attachment region in a protected condition.
FIG. 6B representatively illustrates a top plan view of the absorbent article of FIG. 6A with the posterior attachment region in a fixed donning condition and the anterior attachment region in the protected condition.

Referring now to FIGS. 6A-6D, a top plan view of another exemplary absorbent article 320 in various donning conditions is representatively illustrated. The absorbent article 320 defines a body-facing surface 48 and a garment facing surface 50 (facing away from the viewer in this perspective). The absorbent article 320 includes an anterior attachment region 22 having an anterior body adhesive 62 disposed on the body-facing surface 48. The anterior attachment region 22 also includes an anterior donning system 321 having a first anterior peel strip 322 overlaying a first anterior portion 370 of the anterior body adhesive 62 and a second anterior peel strip 324 overlaying a second anterior portion 371 of the anterior body adhesive 62. Additionally, the anterior attachment region 22 includes an anterior adhesive-free portion 326 that is substantially free of body adhesive. In some embodiments, the anterior adhesive-free portion 326 that is substantially free of body adhesive may completely separate the first anterior portion 370 from the second anterior portion 371 as illustrated in FIG. 6D. In some embodiments, the first anterior peel strip 322 overlaps only the first anterior portion 370 and a part of the anterior adhesive-free portion 326. In these embodiments, the part of the first anterior peel strip 322 that overlaps the anterior adhesive-free portion 326 defines a first anterior finger tab 327. Likewise, in some embodiments, the second anterior peel strip 324 overlaps only the second anterior portion 371 and a part of the anterior adhesive-free portion 326. In these embodiments, the part of the second anterior peel strip 324 that overlaps the anterior adhesive-free portion 326 defines a second anterior finger tab 329. In some embodiments, the first anterior peel strip 322 overlaps the second anterior peel strip 324 to define an anterior overlap region 328. In some embodiments, the second anterior peel strip overlaps the first anterior peel strip to define the anterior overlap region (not shown). In various embodiments, at least a part of the anterior overlap region 328 overlays at least a part of the anterior adhesive-free portion 326. In some embodiments, the anterior overlap region 328 may completely overlay the anterior adhesive-free portion 326.

The absorbent article 320 includes a posterior attachment region 30 having a posterior body adhesive 74 disposed on the body-facing surface 48. The posterior attachment region 30 also includes a posterior donning system 323 having a first posterior peel strip 330 overlaying a first posterior portion 378 of the posterior body adhesive 74 and a second posterior peel strip 332 overlaying a second posterior portion 379 of the posterior body adhesive 74. Additionally, the posterior attachment region 30 includes a posterior adhesive-free portion 334 that is substantially free of body adhesive. In some embodiments, the posterior adhesive-free portion 334 that is substantially free of body adhesive may completely separate the first posterior portion 378 from the second posterior portion 379 as illustrated in FIG. 6D. In some embodiments, the first posterior peel strip 330 overlaps only the first posterior portion 378 and a part of the posterior adhesive-free portion 334. In these embodiments, the part of the first posterior peel strip 330 that overlaps the posterior adhesive-free portion 334 defines a first posterior finger tab 338. Likewise, in some embodiments, the second posterior peel strip 332 overlaps only the second posterior portion 379 and a part of the posterior adhesive-free portion 334. The part of the second posterior peel strip 332 that overlaps the posterior adhesive-free portion 334 defines a second posterior finger tab 340. In some embodiments, the first posterior peel strip 330 overlaps the second posterior peel strip 332 to define a posterior overlap region 336. In some embodiments, the second posterior peel strip overlaps the first posterior peel strip to define a posterior overlap region (not shown). In various embodiments, at least a part of the posterior overlap region 336 overlays at least a part of the posterior adhesive-free portion 334. In some embodiments, the posterior overlap region 336 may completely overlay the posterior adhesive-free portion 334.

The absorbent article 320 of FIGS. 6A-6D facilitates a method for donning an absorbent article via the anterior donning system 321 and the posterior donning system 323. The method includes grasping the first posterior finger tab 338 from the first posterior peel strip 330 overlaying the first posterior portion 378 of the posterior body adhesive 74. For example, the user may grasp the first posterior finger tab 338 between the thumb and forefinger. The method further includes removing the first posterior peel strip 330 to expose the first posterior portion 378 of the posterior body adhesive 74, as illustrated in FIG. 6B. For example, the user may remove the first posterior peel strip 330 by peeling in the longitudinal direction 14. The method further includes attaching the exposed first posterior portion 378 to the posterior part of the body. To attach the first posterior portion 378 to the posterior part of the body without contaminating the adhesive, the user may grasp the area covered by the second posterior peel strip 332 between the thumb and forefinger.

The method further includes the step of grasping the second posterior finger tab 340 from the second posterior peel strip 332 overlaying the second posterior portion 379 of the posterior body adhesive 74 and removing the second posterior peel strip 332 to expose the second posterior portion 379, as illustrated in FIG. 6C. The method then includes attaching the exposed second posterior portion 379 to the posterior part of the body. In some embodiments, the user may peel the second posterior peel strip 332 in the longitudinal direction 14 while smoothing and attaching the second posterior portion 379 to the body at the same time.

The method also includes grasping the first anterior finger tab 327 from the first anterior peel strip 322 overlaying the first anterior portion 370 of the anterior body adhesive 62 and removing the first anterior peel strip 322 to expose the first anterior portion 370, as illustrated in FIG. 6C. For example, the user may grasp the first anterior finger tab 327 between the thumb and forefinger and remove the first anterior peel strip 322 by peeling it off in the longitudinal direction 14 thereby exposing the first anterior portion 370 of the anterior body adhesive 62.

The method also includes attaching the exposed first anterior portion 370 of the anterior body adhesive 62 to the anterior part of the body. To attach the first anterior portion 370 to the anterior part of the body without contaminating the adhesive, the user may grasp the area covered by the second anterior peel strip 324 between the thumb and forefinger. In some embodiments, the method may further include stretching the absorbent article before attaching the exposed first anterior portion 370 to the anterior part of the body. Once the first anterior portion 370 is attached, the method also includes grasping the second anterior finger tab 329 from the second anterior peel strip 324 overlaying the second anterior portion 371 of the anterior body adhesive 62 and removing the second anterior peel strip 324 to expose the second anterior portion 371, as illustrated in FIG. 6D. Finally, the method includes the step of attaching the exposed second anterior portion 371 of the anterior body adhesive 62 to the anterior part of the body. In some embodiments, the user may peel the second anterior peel strip 324 in the longitudinal direction 14 while smoothing and attaching the second anterior portion 371 to the body at the same time.

In some embodiments one or more indicia may be provided on the absorbent article to guide a user in the method of use. For example, referring again to FIG. 6A, a first indicia 352 is provided on the body-facing surface 48 of the first posterior peel strip 330 to signal the first step in one exemplary donning process. In this example, the first indicia 352 include the printed number "1" and a printed arrow to signal that the first step in the exemplary donning process is to peel the first posterior peel strip 330 in the longitudinal direction 14.

Referring now to FIG. 6B, a second indicia 354 is provided on the body-facing surface 48 of the second posterior peel strip 332 to signal the second step in the exemplary donning process. The second indicia 354 include the printed number "2" and a printed arrow to signal that the second step in the exemplary donning process to peel in the direction indicated by the arrow to remove the second posterior peel strip 332 from the posterior attachment region 30. Additionally, a third indicia 356 is provided on the body-facing surface 48 of the first anterior peel strip 322 to signal the third step in the exemplary donning process. The third indicia 356 includes the printed number "3" and a printed arrow to signal that the third step in the exemplary donning process is to remove the first anterior peel strip 322 by peeling the longitudinal direction 14.

Referring now to FIG. 6C, a fourth indicia 358 is provided on the body-facing surface 48 of the second anterior peel strip 324 to signal the fourth step in the exemplary process. The fourth indicia 358 include the printed number "4" and a printed arrow to signal that the fourth step in the exemplary donning process is to remove the second anterior peel strip 324 from the anterior attachment region 22. In various embodiments, the indicia may be visual, tactile, or any other suitable indicators and combinations thereof.

Referring now to FIGS. 7A-7D, a top plan view of an absorbent article 150 in various donning conditions is representatively illustrated. The absorbent article 150 defines a body-facing surface 48 and a garment facing surface 50. The absorbent article 150 includes an anterior attachment region 22 having an anterior body adhesive 62 disposed on the body-facing surface 48. The anterior attachment region 22 also includes an anterior donning system 151 having an anterior peel strip 66 overlaying the anterior body adhesive 62. The anterior peel strip 66 defines a body adhesive facing surface 152 and an opposite surface 154. The opposite surface 154 of the anterior peel strip 66 also includes an anterior anchor 156. Likewise, the absorbent article 150 also includes a posterior attachment region 30 having a posterior body adhesive 74 disposed on the body-facing surface 48. The posterior attachment region 30 also includes a posterior donning system 153 having a posterior peel strip 76 overlaying the posterior body adhesive 74. The posterior peel strip 76 defines a body adhesive facing surface 152 and an opposite surface 154. The opposite surface 154 of the posterior peel strip 76 includes a posterior anchor 158. As used herein, the term "anchor" refers to one or more elements adapted to join two surfaces together. For example, suitable anchors may include, adhesive, cohesive, snaps, hooks, loops, buttons, and the like, and combinations thereof.

Figures 7A, 7B:
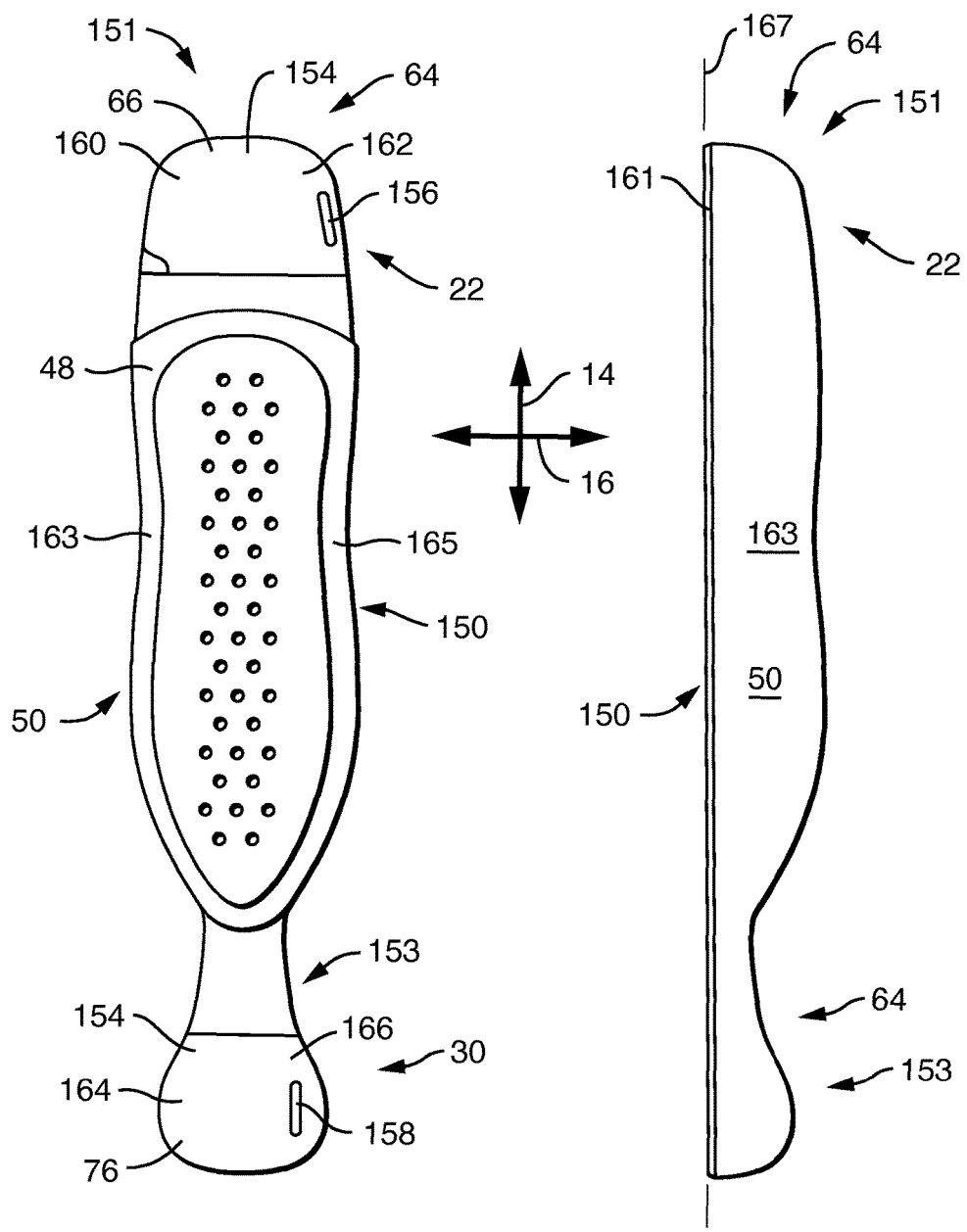
FIG. 7A representatively illustrates a top plan view of another exemplary absorbent article with both the anterior attachment region and the posterior attachment region in a protected condition.
FIG. 7B representatively illustrates a top plan view of the absorbent article of FIG. 7A folded along a longitudinal fold with both the anterior attachment region and the posterior attachment region in the protected condition.

The absorbent article 150 also includes a longitudinal fold 161 as illustrated in FIG. 7B. When the absorbent article 150 is folded along the longitudinal fold 161, a first lateral portion 163 of the absorbent article 150 is folded in facing relation with a second lateral portion 165. In some embodiments, the first lateral portion 163 and the second lateral portion 165 include both the shell 29 and the absorbent component 40. In other words, the entire absorbent article 150 is folded along the longitudinal fold 161 in some embodiments. In some embodiments, the first lateral portion 163 may be the same size as the second lateral portion 165. In these embodiments, the longitudinal fold 161 is generally oriented along the longitudinal centerline 167 of the absorbent article 150 as illustrated in FIG. 7B. Also, when the absorbent article 150 is folded along longitudinal fold 161, a first anterior portion 160 of the opposite surface 154 of the anterior peel strip 66 is attached to a second anterior portion 162 of the opposite surface 154 of the anterior peel strip 66 via the anterior anchor 156. Likewise, when the absorbent article 150 is folded along longitudinal fold 161, a first posterior portion 164 of the opposite surface 154 of the posterior peel strip 76 is attached to a second posterior portion 166 of the opposite surface 154 of the posterior peel strip 76 via the posterior anchor 158.

Thus, when the absorbent article 150 is folded along the longitudinal fold 161 the first lateral portion 163 of the absorbent article 150 is folded upon the second lateral portion 165 of the absorbent article 150. Additionally, a first anterior portion 160 of the opposite surface 154 of the anterior peel strip 66 is attached to a second anterior portion 162 of the opposite surface 154 of the anterior peel strip 66 via the anterior anchor 156. Likewise, when the absorbent article 150 is folded along the longitudinal fold 161 a first posterior portion 164 of the opposite surface 154 of the posterior peel strip 76 is attached to a second posterior portion 166 of the opposite surface 154 of the posterior peel strip 76 via the posterior anchor 158 and defines the protected condition 64.

When the absorbent article 150 is unfolded along the longitudinal fold 161 the first anterior portion 160 of the anterior peel strip 66 remains attached to the second anterior portion 162 via the anterior anchor 156 to define an anterior doubled portion 168. Also, the first posterior portion 164 of the posterior peel strip 76 remains attached to the second posterior portion 166 via the posterior anchor 158 to define a posterior doubled portion 170. Both the anterior attachment region 22 and the posterior attachment region 30 are now in the fixed donning condition 68. In some embodiments, the anterior anchor 156 may be sized and positioned such that anterior doubled portion 168 includes an anterior finger tab 172. Likewise, the posterior anchor 158 may be sized and positioned such that the posterior doubled portion 170 includes a posterior finger tab 174.

The absorbent article 150 illustrated in FIGS. 7A-7D facilitates a method for donning the absorbent article via the anterior donning system 151 and the posterior donning system 153. The method includes unfolding the absorbent article 150 along the longitudinal fold 161 to expose a first posterior portion 78 of the posterior body adhesive 74 and a first anterior portion 70 of the anterior body adhesive 62. In some embodiments, the method may include unfolding the anterior attachment region and the posterior attachment region 30 at generally the same time. Alternately, the anterior attachment region 22 and the posterior attachment region 30 may be unfolded individually to minimize contamination and errant attachment. For example, the method may include unfolding the posterior attachment region 30 first and attaching the posterior attachment region 30 to the body before unfolding the anterior attachment region 22. In yet other example, the method may include unfolding the anterior attachment region 22 first and attaching the anterior attachment region 22 to the body before unfolding the posterior attachment region 30.

Figures 7C, 7D:
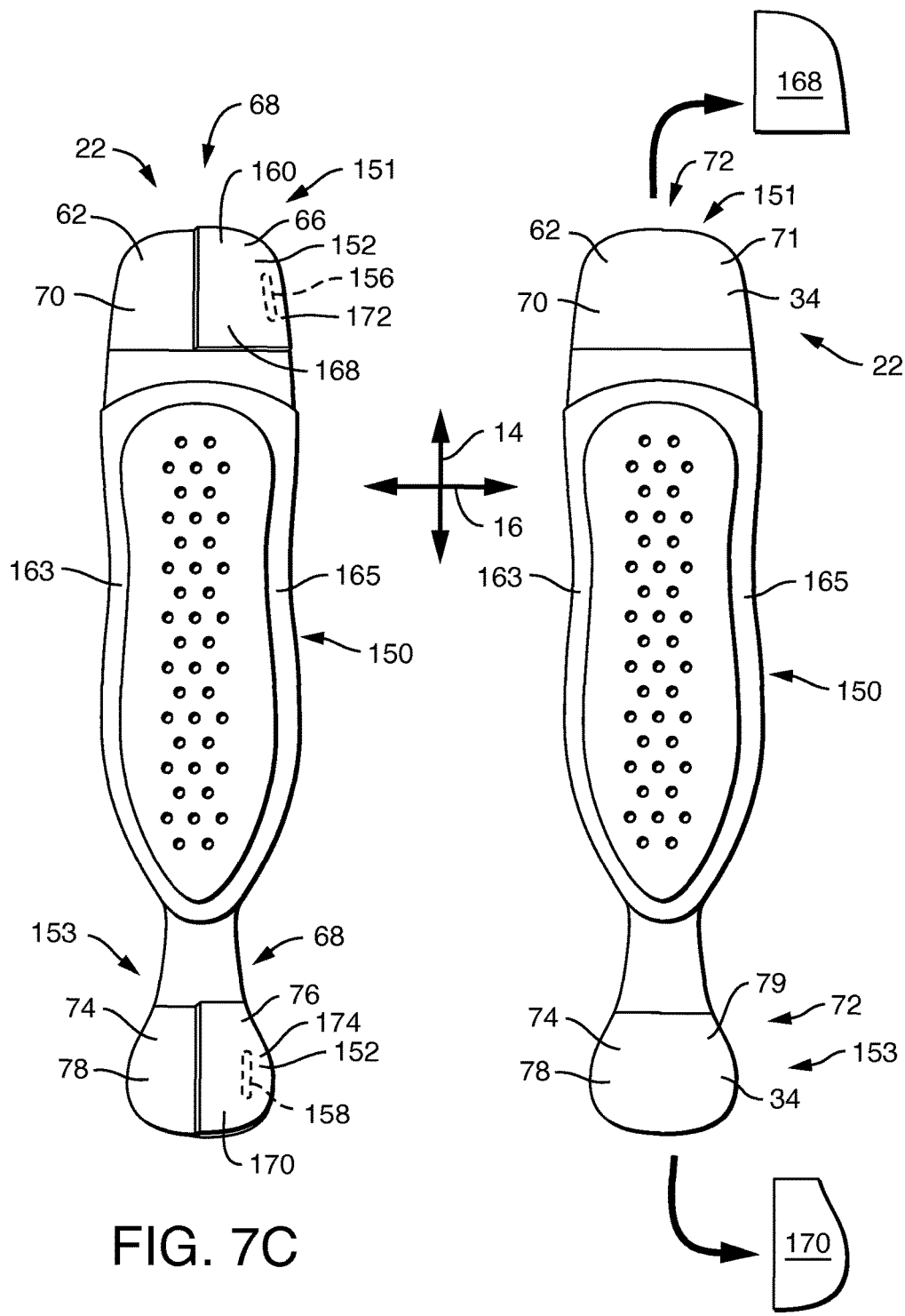
FIG. 7C representatively illustrates a top plan view of the absorbent article of FIG. 7A with both the posterior attachment region and the anterior attachment region in a fixed donning condition.
FIG. 7D representatively illustrates a top plan view of the absorbent article of FIG. 7A with both the posterior attachment region and the anterior attachment region in an exposed condition.

The method further includes grasping the posterior doubled region 170 of the posterior peel strip 76 overlaying the second posterior portion 79 of the posterior body adhesive 74. The method further includes attaching the exposed first posterior portion 78 of the posterior body adhesive 74 to the posterior part of the body. Next the method includes removing the posterior doubled region 170 of the posterior peel strip 76 to expose the second posterior portion 79 of the posterior body adhesive 74 as illustrated in FIG. 7D. The method further includes attaching the exposed second posterior portion 79 to the posterior part of the body. In some embodiments, the method may include grasping the posterior finger tab 174 to assist in the removal of the posterior doubled region 170.

The method also includes grasping the anterior doubled region 168 of the anterior peel strip 66 overlaying the second anterior portion 71 of the anterior body adhesive 62 and attaching the exposed first anterior portion 70 of the anterior body adhesive 62 to the anterior part of the body. In some embodiments, the method may further include the step of stretching and/or positioning the absorbent article 150 before attaching the exposed first anterior portion 70 to the body. Finally, the method includes removing the anterior doubled region 168 of the anterior peel strip 66 to expose the second anterior portion 71 of the anterior body adhesive 62 as illustrated in FIG. 7D. The method further includes attaching the second anterior portion 71 to the anterior part of the body. In some embodiments, the method may include grasping the anterior finger tab 172 to assist in the removal of the anterior doubled region 168.

Referring now to FIGS. 8A-8F, a top plan view of an absorbent article 176 in various donning conditions is representatively illustrated. The absorbent article 176 defines a body-facing surface 48 and a garment facing surface 50. The absorbent article 176 includes an anterior attachment region 22 having an anterior body adhesive 62 disposed on the body-facing surface 48. The anterior attachment region 22 also includes an anterior donning system 182 having an anterior peel strip 66 overlaying the anterior body adhesive 62. The anterior peel strip 66 defines a body adhesive facing surface 152 and an opposite surface 154. The opposite surface 154 of the anterior peel strip 66 also includes one or more anterior anchors. In the illustrated embodiment, the anterior peel strip 66 includes two anterior anchors 156. Likewise, the absorbent article 176 also includes a posterior attachment region 30 having a posterior body adhesive 74 disposed on the body-facing surface 48. The posterior attachment region 30 also includes a posterior donning system 184 having a posterior peel strip 76 overlaying the posterior body adhesive 74. The posterior peel strip 76 defines a body adhesive facing surface 152 and an opposite surface 154. The opposite surface 154 of the posterior peel strip 76 includes one or more posterior anchors. In the illustrated embodiment, the posterior peel strip 76 includes two posterior anchors 158.

Figures 8A, 8B:
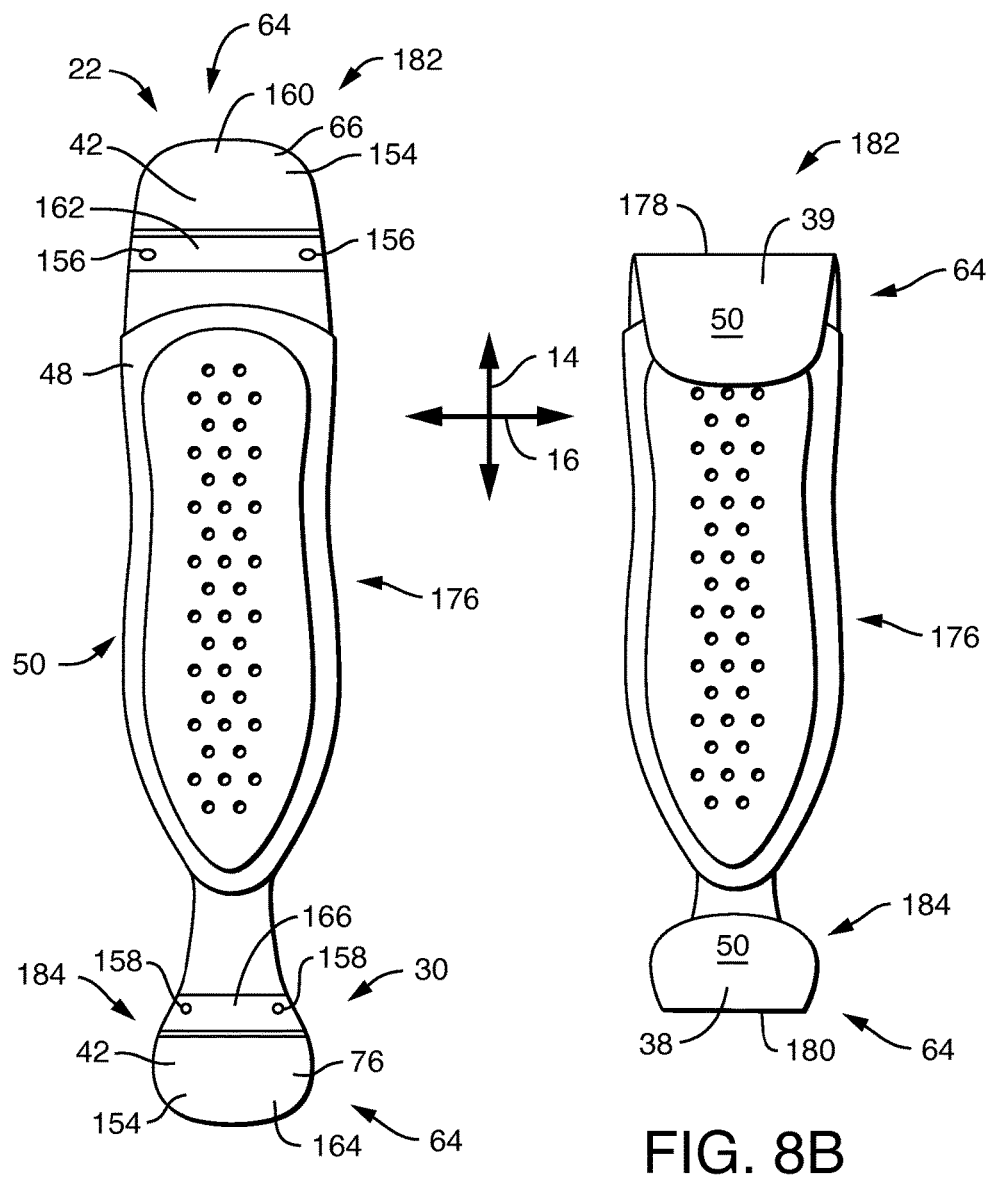
FIG. 8A representatively illustrates a top plan view of another exemplary absorbent article with both the anterior attachment region and the posterior attachment region in a protected condition.
FIG. 8B representatively illustrates a top plan view of the absorbent article of FIG. 8A folded along an anterior lateral fold and a posterior lateral fold.

The absorbent article 176 also includes an anterior lateral fold 178 and a posterior lateral fold 180 as illustrated in FIG. 8B. When the absorbent article 176 is folded along the anterior lateral fold 178, a first anterior portion 160 of the opposite surface 154 of the anterior peel strip 66 is attached to a second anterior portion 162 of the opposite surface 154 of the anterior peel strip 66 via the anterior anchors 156. Likewise, when the absorbent article 176 is folded along the posterior lateral fold 180, a first posterior portion 164 of the opposite surface 154 of the posterior peel strip 76 is attached to a second posterior portion 166 of the opposite surface 154 of the posterior peel strip 76 via the posterior anchors 158.

Thus, when the absorbent article 176 is folded along the anterior lateral fold 178 and along the posterior lateral fold 180, the first anterior portion 160 of the opposite surface 154 of the anterior peel strip 66 is attached to the second anterior portion 162 of the opposite surface 154 of the anterior peel strip 66 via the anterior anchors 156 and defines the protected condition 64. Likewise, when the absorbent article 176 is folded along the posterior lateral fold 180 a first posterior portion 164 of the opposite surface 154 of the posterior peel strip 76 is attached to a second posterior portion 166 of the opposite surface 154 of the posterior peel strip 76 via the posterior anchors 158 and defines the protected condition 64.

Figures 8C, 8D:
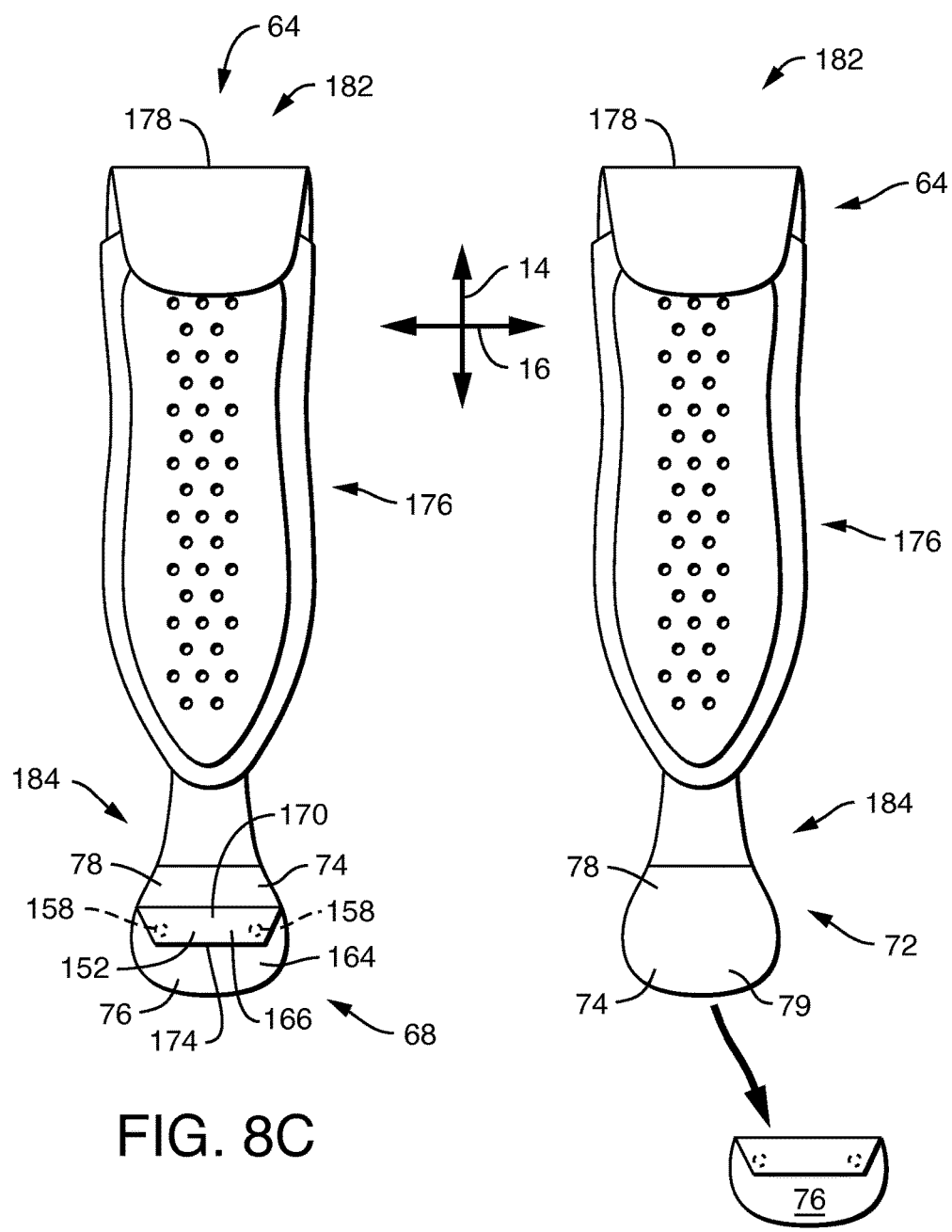
FIG. 8C representatively illustrates a top plan view of the absorbent article of FIG. 8A with the posterior attachment region in a fixed donning condition and the anterior attachment region in a protected condition.
FIG. 8D representatively illustrates a top plan view of the absorbent article of FIG. 8A with the posterior attachment region in an exposed condition and the anterior attachment region in a protected condition.
Figures 8E, 8F:
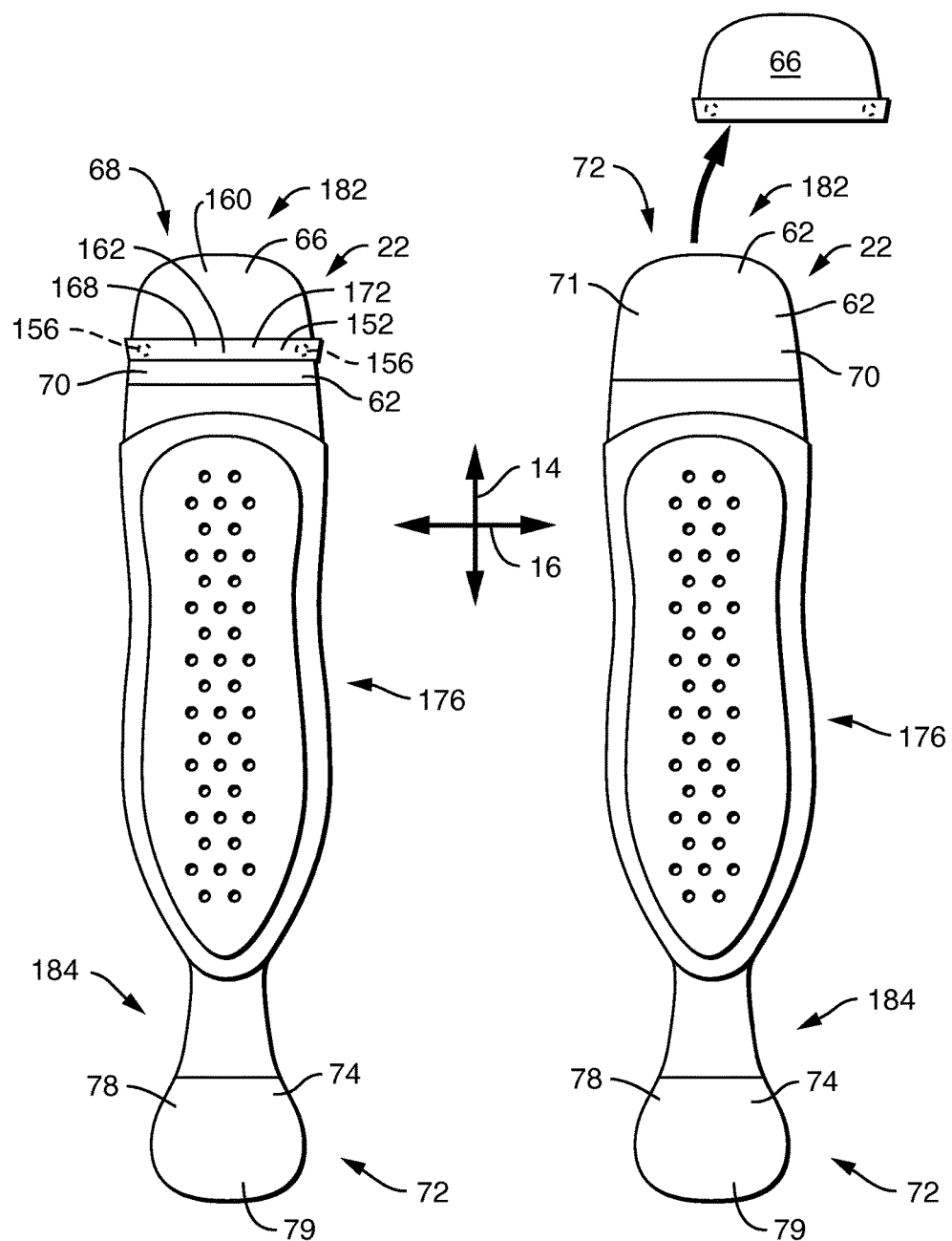
FIG. 8E representatively illustrates a top plan view of the absorbent article of FIG. 8A with the posterior attachment region in an exposed condition and the anterior attachment region in a fixed donning condition.
FIG. 8F representatively illustrates a top plan view of the absorbent article of FIG. 8A with both the posterior attachment region and the anterior attachment region in an exposed condition.

When the absorbent article 176 is unfolded along the anterior lateral fold 178, the second anterior portion 162 of the anterior peel strip 66 remains attached to the first anterior portion 160 to define an anterior doubled portion 168 as illustrated in FIG. 8E. Also, when the absorbent article 176 is unfolded along the posterior lateral fold 180, the second posterior portion 166 of the posterior peel strip 76 remains attached to the first posterior portion 164 to define a posterior doubled portion 170 as illustrated in FIG. 8C. Both the anterior attachment region 22 and the posterior attachment region 30 are now in the fixed donning condition 68. In some embodiments, the anterior anchors 156 may be sized and positioned such that anterior doubled portion 168 includes an anterior finger tab 172. Likewise, the posterior anchors 158 may be sized and positioned such that the posterior doubled portion 170 includes a posterior finger tab 174.

The absorbent article 176 illustrated in FIGS. 8A-8F facilitates a method for donning the absorbent article via the anterior donning system 182 and the posterior donning system 184. The method includes unfolding the absorbent article 176 along the posterior lateral fold 180 to expose a first posterior portion 78 of the posterior body adhesive 74 as illustrated in FIG. 8C. Likewise, the method includes unfolding the absorbent article 176 along the anterior lateral fold 178 to expose a first anterior portion 70 of the anterior body adhesive 62 as illustrated in FIG. 8E. In some embodiments, the method may include unfolding the anterior attachment region and the posterior attachment region 30 at generally the same time. Alternately, the anterior attachment region 22 and the posterior attachment region 30 may be unfolded individually to minimize contamination and errant attachment. For example, the method may include unfolding the posterior attachment region 30 first and attaching the posterior attachment region 30 to the body before unfolding the anterior attachment region 22. In yet another example, the method may include unfolding the anterior attachment region 22 first and attaching the anterior attachment region 22 to the body before unfolding the posterior attachment region 30.

The method further includes grasping the posterior doubled region 170 of the posterior peel strip 76 overlaying the second posterior portion 79 of the posterior body adhesive 74. The method further includes attaching the exposed first posterior portion 78 of the posterior body adhesive 74 to the posterior part of the body. Next the method includes removing the posterior peel strip 76 to expose the second posterior portion 79 of the posterior body adhesive 74 as illustrated in FIG. 8D. The method further includes attaching the exposed second posterior portion 79 to the posterior part of the body. In some embodiments, the method may include grasping the posterior finger tab 174 to assist in the removal of the posterior peel strip 76.

The method also includes grasping the anterior doubled region 168 of the anterior peel strip 66 overlaying the second anterior portion 71 of the anterior body adhesive 62 and attaching the exposed first anterior portion 70 of the anterior body adhesive 62 to the anterior part of the body. In some embodiments, the method may further include the step of stretching and/or positioning the absorbent article 176 before attaching the exposed first anterior portion 70 to the body. Finally, the method includes removing the anterior peel strip 66 to expose the second anterior portion 71 of the anterior body adhesive 62 as illustrated in FIG. 8F. The method further includes attaching the second anterior portion 71 to the anterior part of the body. In some embodiments, the method may include grasping the anterior finger tab 172 to assist in the removal of the anterior peel strip 66.

In some embodiments, only the anterior attachment region of the various absorbent articles may include any of the donning systems disclosed herein. Likewise, in some embodiments, only the posterior attachment region of the various absorbent articles may include any of the donning systems disclosed herein. In some embodiments, both the anterior attachment region and the posterior attachment region may include any of the donning systems disclosed herein. In some embodiments, the anterior attachment region and the posterior attachment region may have any of the donning systems disclosed herein and may have the same donning system. In other embodiments, the anterior attachment region and the posterior attachment region may have any of the donning systems disclosed herein and may have different donning systems.

The product configurations and donning systems disclosed herein are believed to minimize contamination of the body adhesive by providing two distinct grasping surfaces that can be utilized during the attachment process. In addition, these product configurations and donning systems are believed to reduce errant attachment and adhesive fold over by reducing the amount of exposed adhesive during the donning process. Finally, these product configurations and donning systems allow stretching of the absorbent article while the absorbent article is at least partially attached to the body. For example, in some embodiments, the peel strip is an inelastic material and thus inhibits the attachment region from stretching during application which in turn improves the wearer's comfort and the ability of the attachment region to move and stretch with the wearer.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. An absorbent article comprising,
a shell and an absorbent component, wherein the shell defines, in a longitudinal direction, an anterior attachment region, an anterior separation zone, an absorbent component region, a posterior separation zone, and a posterior attachment region, wherein the anterior separation zone separates the anterior attachment region from the absorbent component region and wherein the posterior separation zone separates the posterior attachment region from the absorbent component region;
the anterior attachment region comprising an anterior body adhesive and an anterior adhesive-free portion and defining a protected condition wherein a first anterior peel strip overlays a first anterior portion of the anterior body adhesive and a second anterior peel strip overlays a second anterior portion of the anterior body adhesive and the first anterior peel strip overlaps the second anterior peel strip at the anterior adhesive-free portion; the anterior attachment region being adapted to transition from the protected condition to a fixed donning condition; in the fixed donning condition a portion of the anterior body adhesive is exposed by removal of the first anterior peel strip and a portion of the anterior body adhesive is covered by the second anterior peel strip; the anterior attachment region being adapted to transition from the fixed donning condition to a fully exposed condition; in the fully exposed condition the anterior body adhesive is fully exposed by removal of the second anterior peel strip;
the posterior attachment region comprising a posterior body adhesive and a posterior adhesive-free portion and defining a protected condition wherein a first posterior peel strip overlays a first posterior portion of the posterior body adhesive and a second posterior peel strip overlays a second posterior portion of the posterior body adhesive and the first posterior peel strip overlaps the second posterior peel strip at the posterior adhesive-free portion; the posterior attachment region being adapted to transition from the protected condition to a fixed donning condition; in the fixed donning condition a portion of the posterior body adhesive is exposed by removal of the first posterior peel strip and a portion of the posterior body adhesive is covered by the second posterior peel strip; the posterior attachment region being adapted to transition from the fixed donning condition to a fully exposed condition; in the fully exposed condition the posterior body adhesive is fully exposed by removal of the second posterior peel strip; and
at least one of the anterior separation zone and the posterior separation zone being devoid of absorbent material and body adhesive.

2. The absorbent article of claim 1 wherein the shell defines a shell length, the anterior separation zone defines an anterior separation zone length, the posterior separation zone defines a posterior separation zone length, and at least one of the anterior separation zone length or the posterior separation zone length is at least 5% of the shell length.

3. The absorbent article of claim 2 wherein the shell length is 325 to 350 mm, the anterior separation zone length is 5 to 15 mm, and the posterior separation zone length is 20 to 50 mm.

4. The absorbent article of claim 3 wherein the anterior separation zone is elastic, the posterior separation zone is elastic, the anterior attachment region is inelastic, and the posterior attachment region is inelastic.

5. An absorbent article comprising,
a shell and an absorbent component, wherein the shell defines, in a longitudinal direction, an anterior attachment region, an anterior separation zone, an absorbent component region, a posterior separation zone, and a posterior attachment region, wherein the anterior separation zone separates the anterior attachment region from the absorbent component region and wherein the posterior separation zone separates the posterior attachment region from the absorbent component region; wherein the absorbent article defines a body-facing surface and a garment-facing surface;
the anterior attachment region comprising an anterior body adhesive disposed on the body-facing surface and defining a protected condition wherein an anterior peel strip overlays the anterior body adhesive, the anterior peel strip defining a body adhesive facing surface and an opposite surface wherein an anterior anchor is attached to the opposite surface of the anterior peel strip and wherein the anterior attachment region comprises a longitudinal fold wherein a first anterior portion of the opposite surface of the anterior peel strip is attached to a second anterior portion of the opposite surface of the anterior peel strip via the anterior anchor to define the protected condition; the anterior attachment region being adapted to transition from the protected condition to a fixed donning condition; in the fixed donning condition a portion of the anterior body adhesive is exposed and a portion of the anterior body adhesive is covered by the anterior peel strip; the anterior attachment region being adapted to transition from the fixed donning condition to a fully exposed condition; in the fully exposed condition the anterior body adhesive is fully exposed;
the posterior attachment region comprising a posterior body adhesive disposed on the body-facing surface and defining a protected condition wherein a posterior peel strip overlays the posterior body adhesive, the posterior peel strip defining a body adhesive facing surface and an opposite surface, wherein a posterior anchor is attached to the opposite surface of the posterior peel strip and wherein the posterior attachment region comprises a longitudinal fold wherein a first posterior portion of the opposite surface of the posterior peel strip is attached to a second posterior portion of the opposite surface of the posterior peel strip via the posterior anchor to define the protected condition; the posterior attachment region being adapted to transition from the protected condition to a fixed donning condition; in the fixed donning condition a portion of the posterior body adhesive is exposed and a portion of the posterior body adhesive is covered by posterior peel strip; the posterior attachment region being adapted to transition from the fixed donning condition to a fully exposed condition; in the fully exposed condition the posterior body adhesive is fully exposed; and at least one of the anterior separation zone and the posterior separation zone being devoid of absorbent material and body adhesive.

6. The absorbent article of claim 5 wherein the shell defines a shell length, the anterior separation zone defines an anterior separation zone length, the posterior separation zone defines a posterior separation zone length, and at least one of the anterior separation zone length or the posterior separation zone length is at least 5% of the shell length.

7. The absorbent article of claim 5 wherein the shell length is 325 to 350 mm, the anterior separation zone length is 5 to 15 mm, and the posterior separation zone length is 20 to 50 mm.

8. The absorbent article of claim 5 wherein the anterior separation zone is elastic, the posterior separation zone is elastic, the anterior attachment region is inelastic, and the posterior attachment region is inelastic.

9. An absorbent article comprising,
a shell and an absorbent component, wherein the shell defines, in a longitudinal direction, an anterior attachment region, an anterior separation zone, an absorbent component region, a posterior separation zone, and a posterior attachment region, wherein the anterior separation zone separates the anterior attachment region from the absorbent component region and wherein the posterior separation zone separates the posterior attachment region from the absorbent component region; wherein the absorbent article defines a body-facing surface and a garment-facing surface;

the anterior attachment region comprising an anterior body adhesive disposed on the body-facing surface and defining a protected condition wherein an anterior peel strip overlays the anterior body adhesive, the anterior peel strip defining a body adhesive facing surface and an opposite surface wherein an anterior anchor is attached to the opposite surface of the anterior peel strip and wherein the anterior attachment region comprises an anterior lateral fold wherein a first portion of the absorbent article in the anterior region is folded upon a second portion of the absorbent article in the anterior region along the anterior lateral fold and a first portion of the opposite surface of the anterior peel strip is attached to a second portion of the opposite surface of the anterior peel strip via the anterior anchor; the anterior attachment region being adapted to transition from the protected condition to a fixed donning condition; in the fixed donning condition a portion of the anterior body adhesive is exposed and a portion of the anterior body adhesive is covered by the anterior peel strip; the anterior attachment region being adapted to transition from the fixed donning condition to a fully exposed condition; in the fully exposed condition the anterior body adhesive is fully exposed;

the posterior attachment region comprising a posterior body adhesive disposed on the body-facing surface and defining a protected condition wherein a posterior peel strip overlays the posterior body adhesive, the posterior peel strip defining a body adhesive facing surface and an opposite surface, wherein a posterior anchor is attached to the opposite surface of the posterior peel strip and wherein the posterior attachment region comprises a posterior lateral fold wherein a first portion of the absorbent article in the posterior region is folded upon a second portion of the absorbent article in the posterior region along the posterior lateral fold and a first portion of the opposite surface of the posterior peel strip is attached to a second portion of the opposite surface of the posterior peel strip via the posterior anchor; the posterior attachment region being adapted to transition from the protected condition to a fixed donning condition; in the fixed donning condition a portion of the posterior body adhesive is exposed and a portion of the posterior body adhesive is covered by the posterior peel strip; the posterior attachment region being adapted to transition from the fixed donning condition to a fully exposed condition; in the fully exposed condition the posterior body adhesive is fully exposed; and at least one of the anterior separation zone and the posterior separation zone being devoid of absorbent material and body adhesive.

10. The absorbent article of claim 9 wherein the shell defines a shell length, the anterior separation zone defines an anterior separation zone length, the posterior separation zone defines a posterior separation zone length, and at least one of the anterior separation zone length or the posterior separation zone length is at least 5% of the shell length.

11. The absorbent article of claim 9 wherein the shell length is 325 to 350 mm, the anterior separation zone length is 5 to 15 mm, and the posterior separation zone length is 20 to 50 mm.

12. The absorbent article of claim 9 wherein the anterior separation zone is elastic, the posterior separation zone is elastic, the anterior attachment region is inelastic, and the posterior attachment region is inelastic.

13. An absorbent article defining a body-facing surface and a garment-facing surface and comprising at least one anterior attachment region or posterior attachment region wherein
the anterior attachment region comprises an anterior body adhesive disposed on the body-facing surface and a first anterior peel strip overlaying a first anterior portion of the anterior body adhesive and a second anterior peel strip overlaying a second anterior portion of the anterior body adhesive, wherein the anterior attachment region includes an anterior adhesive-free portion and wherein the first anterior peel strip overlaps the second anterior peel strip at the anterior adhesive-free portion; or
the posterior attachment region comprises a posterior body adhesive disposed on the body-facing surface and a first posterior peel strip overlaying a first posterior portion of the posterior body adhesive and a second posterior peel strip overlaying a second posterior portion of the posterior body adhesive, wherein the posterior attachment region includes a posterior adhesive-free portion and wherein the first posterior peel strip overlaps the second posterior peel strip at the posterior adhesive-free portion.

14. The absorbent article of claim 13 comprising both the anterior attachment region and the posterior attachment region.

15. An absorbent article defining a body-facing surface and a garment-facing surface and comprising, an anterior attachment region having an anterior body adhesive disposed on the body-facing surface and having an anterior peel strip overlaying the anterior body adhesive wherein the anterior peel strip defines a body adhesive facing surface and an opposite surface and wherein the opposite surface includes an anterior anchor;

a posterior attachment region having a posterior body adhesive disposed on the body-facing surface and having a posterior peel strip overlaying the posterior body adhesive wherein the posterior peel strip defines a body adhesive facing surface and an opposite surface and wherein the opposite surface includes a posterior anchor;

a first lateral portion comprising a shell and an absorbent component and a second lateral portion comprising the shell and the absorbent component; and a longitudinal fold wherein the first lateral portion is in facing relation with the second lateral portion and a first anterior portion of the opposite surface of the anterior peel strip is attached to a second anterior portion of the opposite surface of the anterior peel strip via the anterior anchor and wherein a first posterior portion of the opposite surface of the posterior peel strip is attached to a second posterior portion of the opposite surface of the posterior peel strip via the posterior anchor.

16. An absorbent article defining a body-facing surface and a garment-facing surface and comprising at least one anterior attachment region or posterior attachment region wherein, the anterior attachment region comprises an anterior body adhesive disposed on the body-facing surface, an anterior peel strip overlaying the anterior body adhesive, and an anterior lateral fold, wherein the anterior peel strip defines a body adhesive facing surface and an opposite surface, wherein the opposite surface includes an anterior anchor, and wherein a first anterior portion of the anterior peel strip is attached to a second anterior portion of the opposite surface of the anterior peel strip via the anterior anchor; or the posterior attachment region comprises a posterior body adhesive disposed on the body-facing surface, a posterior peel strip overlaying the posterior body adhesive, and a posterior lateral fold, wherein the posterior peel strip defines a body adhesive facing surface and an opposite surface, wherein the opposite surface includes a posterior anchor; and wherein a first posterior portion of the anterior peel strip is attached to a second posterior portion of the opposite surface of the posterior peel strip via the posterior anchor.

17. The absorbent article of claim 16 further comprising a shell and an absorbent component, wherein the shell defines, in a longitudinal direction, the anterior attachment region, an anterior separation zone, an absorbent component region, a posterior separation zone, and the posterior attachment region, wherein the anterior separation zone separates the anterior attachment region from the absorbent component region and wherein the posterior separation zone separates the posterior attachment region from the absorbent component region, and wherein at least one of the anterior separation zone and the posterior separation zone being devoid of absorbent material and body adhesive.

18. The absorbent article of claim 16 comprising both the anterior attachment region and the posterior attachment region.

* * * * *